United States Patent [19]

Bacus et al.

[11] Patent Number: 4,998,284
[45] Date of Patent: Mar. 5, 1991

[54] DUAL COLOR CAMERA MICROSCOPE AND METHODOLOGY FOR CELL STAINING AND ANALYSIS

[75] Inventors: James W. Bacus, Hinsdale; Ralph S. Hernicz, Elk Grove Village, both of Ill.

[73] Assignee: Cell Analysis Systems, Inc., Lombard, Ill.

[21] Appl. No.: 315,443

[22] Filed: Feb. 24, 1989

Related U.S. Application Data

[63] Continuation-in-part of Ser. No. 121,674, Nov. 17, 1987, which is a continuation-in-part of Ser. No. 927,285, Nov. 4, 1986, abandoned, which is a continuation-in-part of Ser. No. 794,937, Nov. 4, 1985, Pat. No. 4,741,043.

[51] Int. Cl.$^5$ .............................................. G06K 9/00
[52] U.S. Cl. ........................................... 382/6; 382/1; 358/101; 358/39
[58] Field of Search ................. 381/1, 6; 358/101, 39; 250/573, 564, 565; 356/39, 244, 256

[56] References Cited

U.S. PATENT DOCUMENTS

| | | | |
|---|---|---|---|
| 3,297,879 | 1/1963 | Meyer | 250/237 |
| 3,481,659 | 12/1969 | Rosenberg | 350/94 |
| 3,532,412 | 10/1970 | Miller | 350/95 |
| 3,773,425 | 11/1973 | Bentley | 356/191 |
| 3,847,486 | 11/1974 | McCabe | 356/205 |
| 3,851,156 | 11/1974 | Green | 235/151.3 |
| 3,895,854 | 7/1975 | Ziffer | 350/20 |
| 3,907,437 | 9/1975 | Hirschfeld | 356/39 |
| 3,977,791 | 8/1976 | Weber et al. | 356/168 |
| 4,000,417 | 12/1976 | Adkisson et al. | 356/39 |
| 4,017,192 | 4/1977 | Rosenthal | 356/39 |
| 4,045,772 | 8/1977 | Bouton et al. | 340/146.3 |
| 4,048,616 | 9/1977 | Hart et al. | 340/146.3 |
| 4,061,914 | 12/1977 | Green | 250/201 |
| 4,097,845 | 6/1978 | Bacus | 340/146.3 |
| 4,125,828 | 11/1978 | Resnick et al. | 340/146.3 |
| 4,129,854 | 12/1978 | Suzuki et al. | 340/146.3 |
| 4,132,767 | 1/1979 | Tohmatsu et al. | 424/1 |
| 4,152,410 | 5/1979 | Ishii | 424/1 |
| 4,160,817 | 7/1979 | Bucovaz et al. | 424/1 |
| 4,174,178 | 11/1979 | Ouchi et al. | 356/39 |
| 4,175,860 | 11/1979 | Bacus | 356/39 |
| 4,199,748 | 4/1980 | Bacus | 340/146.3 |
| 4,207,554 | 6/1980 | Resnick et al. | 340/146.3 |
| 4,213,036 | 7/1980 | Kopp et al. | 235/92 |
| 4,219,440 | 8/1980 | Runck et al. | 252/408 |
| 4,227,814 | 10/1980 | Soodak et al. | 356/410 |
| 4,231,660 | 11/1980 | Remy et al. | 356/244 |
| 4,232,001 | 11/1980 | Jensen et al. | 424/1 |
| 4,232,970 | 11/1980 | Sawamura et al. | 356/432 |
| 4,257,709 | 3/1981 | Mostyn, Jr. | 356/435 |
| 4,307,376 | 12/1981 | Miller et al. | 340/146 |
| 4,362,386 | 12/1982 | Matsushita et al. | 356/39 |
| 4,389,669 | 6/1983 | Epstein et al. | 358/101 |
| 4,404,683 | 9/1983 | Kobayashi et al. | 382/6 |
| 4,408,231 | 10/1983 | Bushaw et al. | 358/280 |
| 4,446,871 | 5/1984 | Imura | 128/633 |
| 4,453,266 | 6/1984 | Bacus | 382/6 |
| 4,513,438 | 8/1985 | Graham et al. | 382/6 |
| 4,523,278 | 6/1985 | Reinhardt et al. | 364/413 |
| 4,562,593 | 12/1985 | Ooe et al. | 382/6 |
| 4,592,089 | 5/1986 | Hartman | 382/6 |
| 4,741,043 | 4/1988 | Bacus | 382/6 |

FOREIGN PATENT DOCUMENTS

59-88716  5/1984  Japan.

OTHER PUBLICATIONS

King and Green, "Monoclonal Antibodies Localize Oestrogen Receptor in the Nuclei of Target Cells", Nature, 307:745-747, 1984.

(List continued on next page.)

Primary Examiner—David K. Moore
Assistant Examiner—Michael Razavi
Attorney, Agent, or Firm—Fitch, Even, Tabin & Flannery

[57] ABSTRACT

A method and apparatus is disclosed for use in performing automated classification of cells and other microscopic specimens. The apparatus provides a compact, adjustable assembly that is operable to provide: an operator-apparatus interactive classification system for the cell analysis; alternative techniques for different cells, cytoplasms and cell populations; and enhanced image or color separation and analysis.

55 Claims, 20 Drawing Sheets

OTHER PUBLICATIONS

Jensen et al., "Receptors Reconsidered: A 20-Year Perspective", *Recent Progress in Hormone Research*, 38:1-39.

Green et al., "Monoclonal Antibodies to Human Estrogen Receptor", *Proc., Natl. Acad. Sci. USA*, 77:5115-5119, 1980.

James and Goldstein, "Haemoglobin Content of Individual Erythrocytes in Normal and Abnormal Blood", *British Journal of Haemotology*, 28:89-102, 1974.

McCarty et al., "Estrogen Receptor Analyses", *Arch Pathol Lab Med*, 109:716-721, 1985.

"Immunocytochemical Assay for the Detection of Human Estrogen Receptor", Abbott Laboratories, 83-1547/R2, 1986.

Sherrod and Taylor, "Nonlymphocyte Tumor Markers in Tissues", *Immunopathology and Immunohistology*, Chapter 145, pp. 938-947.

King et al., "Comparison of Immunocytochemical and Steriod-Binding Assays for Estrogen Receptor in Human Breast Tumors", *Cancer Research*, 45:293-294, 1985.

Thorell, B., "Cell Studies with Microspectrography", pp. 95-119.

QUANTITIVE IMMUNOPLOIDY ANALYSIS
CALIBRATION SCREEN
 USE RED FILTER
 PATIENT IDENTIFICATION JOHN DOE
 ACCESSION NUMBER    987654321
 DNA INDEX BASED ON 7.18 PICOGRAMS

DATE: 17/NV/87  TIME: 15:02:33

CALIBRATION DATA
LIGHT LEVEL  130
CELL COUNT        20
PEAK VALUE     10600

MEASURE OPERATIONS    0
0 = ACCEPT CELL
9 = REJECT CELL
<CR> = STOP/SAVE DATA
<ESC> = STOP
CTRL F1 = BACKUP
CTRL F2 = NEXT
CTRL F3 = AUTOMATIC
CTRL F6 = FORWARD

CK-LIGHT

SET-XY

FOCUS

MEASURE

XY

ANALYZE

CLEAR-ALL

HELP

MAIN

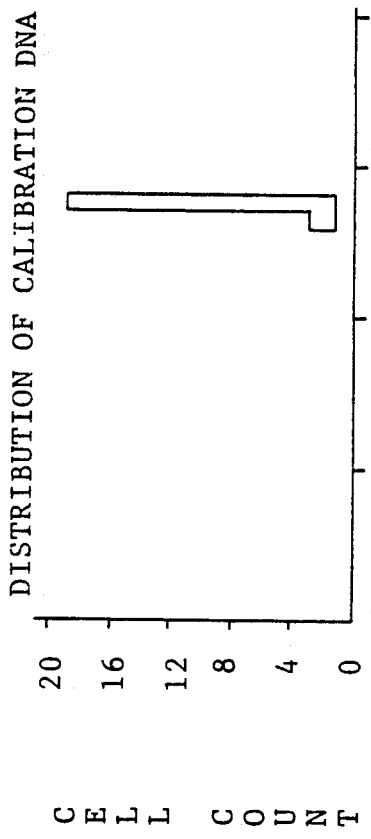

fig.15

DUAL COLOR CAMERA MICROSCOPE AND METHODOLOGY FOR CELL STAINING AND ANALYSIS

RELATED APPLICATIONS

This application is a continuation-in-part of co-pending U.S. patent application Ser. No. 121,674, filed on Nov. 17, 1987, in the names of James W. Bacus and Robert J. Marder, which was entitled "Methods and Apparatus for Immunoploidy Analysis"; which in turn is a continuation-in-part of application U.S. Ser. No. 927,285, filed Nov. 4, 1986 now abandoned in the name of James W. Bacus, and entitled "Analysis Method and Apparatus for Biological Specimens"; which is a continuation-in-part of application U.S. Ser. No. 794,937 filed Nov. 4, 1985, now U.S. Pat. No. 4,741,043 in the name of James W. Bacus and entitled "Method of And An Apparatus for Image Analyses of Biological Specimens"; all of which are commonly assigned with the present application. These previous disclosures are hereby expressly incorporated by reference herein.

FIELD OF THE INVENTION

The present invention generally relates to an apparatus for the measurement of cell object features, such as morphology and mass, and a methodology to enhance cell structures for quantitative measurement methods utilizing this apparatus. The present apparatus finds particular application in studies on cell structures in the field of pathology, which may include human tissue for cancer research or diagnosis.

In the pathology laboratory, visual observation is the present method for examining cells and tissue. The shape and texture of suspected cancer cells are observed, after staining to contrast and enhance the cells, by a pathologist, primarily through a microscope, who then classifies these cells into a normal category, or one of several abnormal or possibly cancerous categories. Such evaluations are very subjective and do not always differentiate or precisely quantify small changes in DNA, proteins or other substances within individual cells or in very small populations of abnormal cells. For example, these small changes may represent an incipient stage of cancer or a change in cell structure due to treatment of such cancer by chemotherapy or radiation. Therefore, small changes are important in the diagnosis and prognosis of any such diseases.

The pathologist, viewing a stained specimen under a microscope, possesses the discerning expertise of a person skilled in classifying cells as normal or abnormal, who can thus proffer a diagnosis and/or prognosis. The experienced pathologist is able to make relatively quick, infinite gradations of classifications as "almost normal", "slightly abnormal", etc. On the other hand, the classification and measurement of cell features and parameters manually by a pathologist on a cell-by-cell basis is extremely tedious and time-consuming. Statistical analysis of cell data taken by hand is relatively difficult, as each record has to be individually entered and processed. For different records or analyses, which are taken at different times, as well as under varying conditions, broad statistical categorizations may be unreliable.

Alternatively, automatic cell analysis provides the pathologist with specialized equipment to perform an analysis. In automatic cell analysis, for example, a flow cytometer, mass tests are performed in gross on a specimen cell population without exclusion or inclusion of distinguishing population data thereof. The specimen is measured "as is" without knowledge of what cells or how many cells are being measured. Important single-cell data or data from relatively small groups of cells is lost in the overall averaging of such a specimen. Further, such automatic tests frequently require relatively large specimen samples, and the sample is frequently destroyed or consumed.

There are commercially available, general purpose, flow cytometers. However, they are extremely expensive and can handle only liquid blood specimens or tissue desegregation. These cytometers are incapable of working on standard tissue sections or using conventional microscope slides, which are the preferred specimen formats of pathology laboratories. Additionally, a flow cytometer precludes the analysis of cell morphology, such as texture, size and shape of cell nuclei.

Optical enhancement of cell cytoplasm for different types of cells is, in some cases, incompatible with current DNA staining technique. That is, the optical enhancement factor or stain technique for the cytoplasm should be compatible with the imaging technique for computer analysis of optical density while simultaneously not impairing the sensitivity of the imaging techniques for the nuclear staining. In the example of Feulgen staining, the optical enhancement of cytoplasm after Feulgen staining of the DNA is not practicable as the Feulgen process uses highly acidic reagents, which may destroy other optical enhancement factors or stains. A further limiting factor or requirement is that any staining done prior to a Feulgen or DNA-marking stain cannot disrupt or negatively affect the nuclear material, which might detrimentally affect the subsequent nuclear marking stain.

Therefore, one of the main thrusts of continuing research is the development of stains and staining techniques, which will provide distinguishable optical enhancement or marking of the separate components of cells, for example, the cytoplasm and nuclear DNA, without interfering with the image analysis of the other components. As a practical matter, however, the distinguished components of the cells without the means to analyze these separate characteristics, is of minimal value, although it certainly would be an asset. Therefore, it is necessary to provide the chemical compositions and components to distinguish the characteristics of the various cell components, and to provide the mechanical equipment and electronic networks to analyze the distinguished cell components. Earlier disclosed structures were adequate for transferring and communicating the image to the processing network, however, it is desirable to minimize the physical structure, or at least the apparatus size, for improved manufacture and esthetic appearance, as well as improving the means for calibration and utilization of the available light energy of the image.

In the above-identified patent application Ser. No. 121,674, there is disclosed a system that performs a two-color assay such as an immunoperoxidase staining of nuclear antigens, using a pair of optical filters which are manually shifted to perform a serial analysis of each one of the two stained materials.

The present invention is directed to the elimination of the need to change filters, which is a relatively slow system and is subject to operator error. For example, should the operator forget to shift from the first filter to the next filter, or if he does not operate the filters in the proper sequence, the resulting measurements would be in error. The time needed for manual shifts of filters slows down the process relative to a two-color, simultaneous analysis. More specifically, the processing and analysis rate are enhanced when two colors are simultaneously rather than sequentially analyzed, as is the technique with the two-color, manual filtering system. As a result of using a dual-color simultaneous analytic technique, the results of the analysis are more quickly available t the viewer and the software programs are easier to use.

Programs currently available for use with the dual color analysis include cell population identification and DNA measurement of cell nuclei, called a ploidy analysis. Another program evaluates nuclear antigens stained by immunoperoxidase methods, such as estrogen or progesterone receptor assays, to provide a quantitative nuclear antigen measurement. A third program provides a quantitative proliferation index for measuring proliferation in either cells or tissues by using immunoperoxidase staining techniques with an antibody to proliferated cells. This proliferation index is fully described in a co-pending application filed of even date entitled "Method of and Apparatus for Measuring Proliferation" by James Bacus et al. The dual color system of this invention is also used to perform the cell measurement described in the above-referenced patent applications.

The present invention provides an inexpensive and easily adjustable dual-color sensor system, which aligns and focuses chemically-optically enhanced images of cells and/or materials thereon for viewing by a person; and, for making precise quantitative measurements of the stained materials associated with the cells. Chromogens used in staining are wide band spectra emitters rather than narrow band spectra emitters, and consequently interference between their respective spectrums is a problem to be overcome. Glare is also present, which tends to add light that interferes with precise optical density measurements, and this problem must also be overcome. Good spectral contrast in a stained cell enhances the ability to quantify small changes in DNA proteins or other substances, and this makes it possible to provide the required precision quantitative measurements. Also, signal measurements contain significant electrical noise, which must be removed during electronic processing. This noise deletion is especially required where the signal intensity is not maximized by taking optical density measurements at a measured wavelength. Hence, it is desirable make narrow band wavelength measurements for the respective optical densities at each of two specifically different narrow band wavelengths that do not overlap or interfere with each other.

The present invention provides a method and apparatus that will successfully perform a two-color analysis, for example, a Feulgen staining technique for the immunoploidy analysis which classifies cells based on a blue color for DNA in the nucleus and a red chromogen for monoclonal antibodies. In an ionic staining technique, a methyl green staining agent is used to combine with a cell component in the nucleus and a Diaminobenzidene (Peroxidase-monoclonal antibody) combines with a component in the cytoplasm. In a third staining technique, the methyl green is used to combine with the cell component in the nucleus and a red chromogen with alkali phosphatase combines with a cell component in the cytoplasm. Also, in oncogene products it is possible to measure estrogen or progesterone receptors for nuclear analysis and antibodies to measure materials in the cytoplasm. Other combinations of stain materials to mark the components of the cell, that is nucleus or cytoplasm, may be used. In each instance, there is a need to separate the emission or transmission spectrums for the respective stains and, as will be explained, to match the filters for them.

SUMMARY OF THE INVENTION

The present invention provides methods and apparatus for the measurement of selected features and parameters of cells in a cell population by the optical identification of their type, as well as their morphology. Earlier apparatus measured the DNA content of selected cells of a subpopulation selected from a cell specimen, which subpopulation was based on the optical marking of certain cells therein.

The present apparatus and techniques further enhance and improve earlier methods and apparatus, as they provide: (1) alternative staining and analytic techniques for different cells, cytoplasms and cell populations; (2) enhanced image or color separation for greater distinguishment by the image processing equipment; (3) a compact, efficient and easily-adjusted image acquisition apparatus to further enhance the image equality and accuracy of the image processing techniques; and, (4) an apparatus for parallel image processing as opposed to the presently available serial image processors. These characteristics thus provide an improved calibration and image processing technique for the analysis of cells or other materials, either biological or inorganic, by image analysis techniques; improve both the method and apparatus for quantitative ploidy analysis of cells through improved image pattern recognition equipment; and provide an enhanced equipment package, which is both visually more appealing and less obtrusive, as well as providing a more technically accurate and efficient utilization of available light energy.

In addition, the improved apparatus has narrow bandpass filtering to reduce glare as well as specific narrow bandpass filters to distinguish the spectra for the monochromatic camera and not the standard RGB, solid state television sensors frequently utilized in these apparatus. The structure eliminates the need to mechanically move either the filters or sample position for review of different cell components and it is readily adaptable to or operable with cell-component stains and staining techniques.

These and other features and objects of the invention will become more readily apparent from the following description of the drawings and the preferred embodiment.

BRIEF DESCRIPTION OF THE DRAWINGS

In the Figures of the drawings, like reference numerals identify like components, and in the drawings:

FIGS. 1-A-1-D illustrate different histograms for aneuploidy analysis;

FIG. 15 is a pictorial representation of a calibration screen appearing on the instruction monitor illustrated in FIG. 1;

DETAILED DESCRIPTION OF THE PREFERRED EMBODIMENT

Apparatus Structure

The apparatus specifically illustrated in FIGS. 3 and 23-28 and the methods described herein can be utilized to develop histograms and other statistical data of cell populations, which may find particular application in the diagnosis and prognosis of diseases. A specific example of this analysis capability is the quantity and distribution of the nuclear DNA, including the distinguishment of particular proteins at protein sites and the DNA nucleus.

The apparatus of FIGS. 23-28 has fewer reflective or refractive surfaces for light impingement than previous structures, thus minimizing light beam attenuation. The ease of adjustment of the light beam or light beam path assists in focusing the video cameras while providing more efficient use of the available light.

Figure 1:
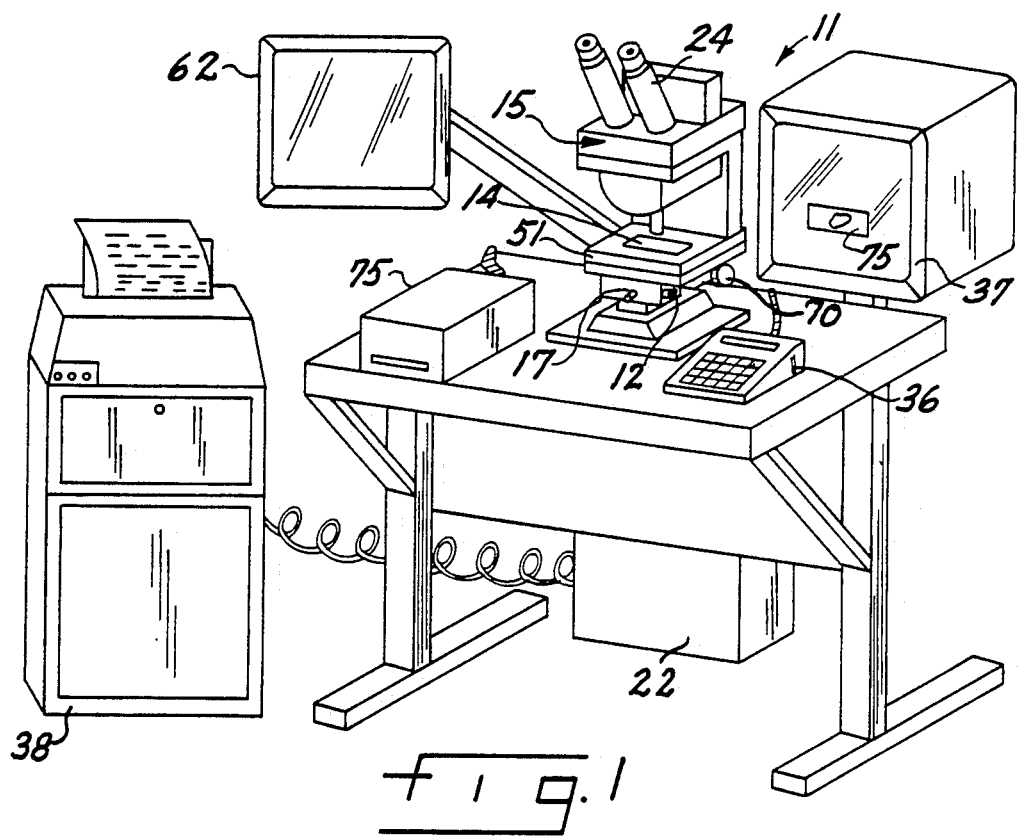
FIG. 1 is a pictorial representation of an image analysis system constructed in accordance with the invention.
Figure 2:
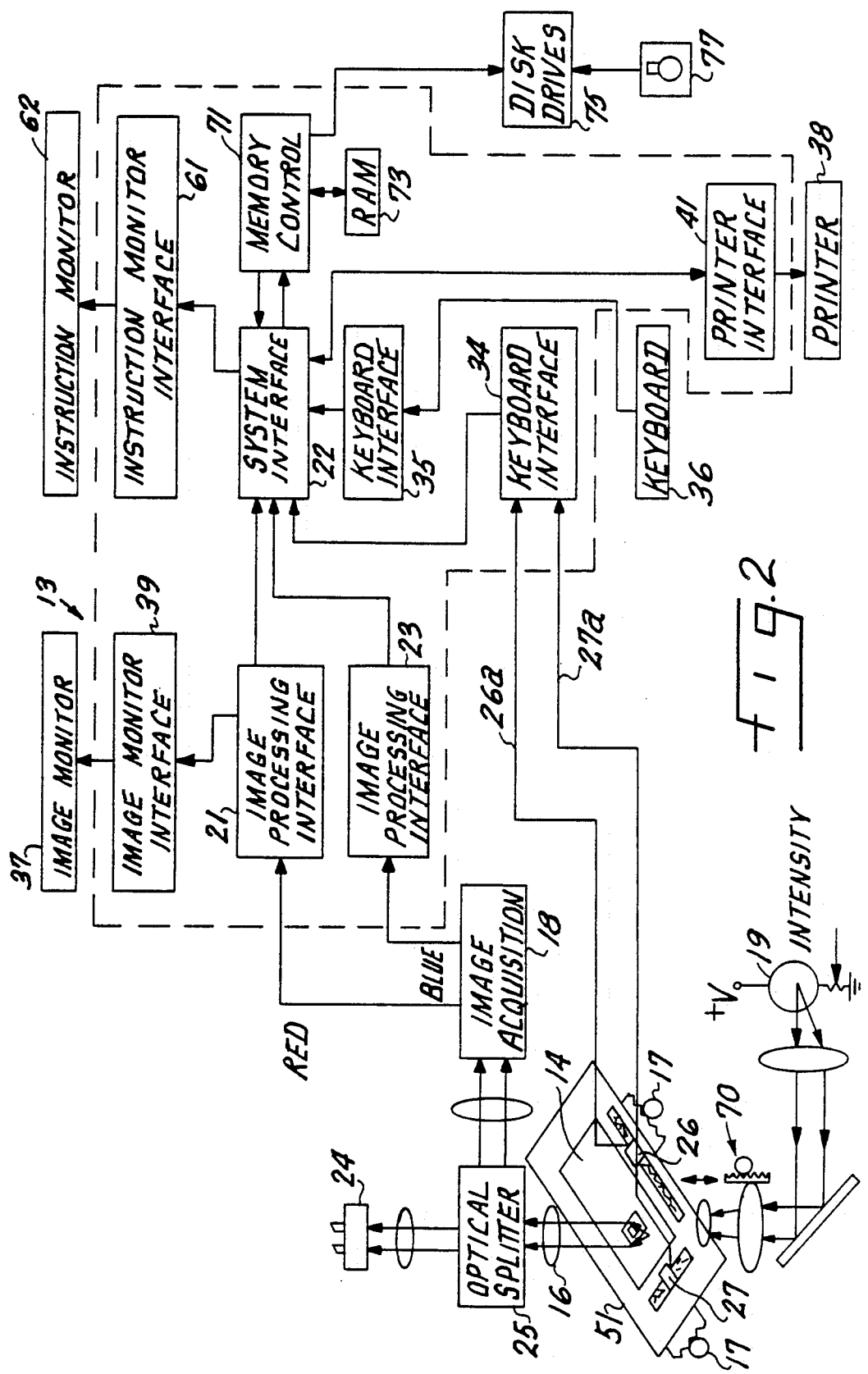
FIG. 2 is a functional block diagram of the image analysis system illustrated in FIG. 1, which is adapted to perform the quantitation methods for nuclear DNA in accordance with the invention.

In FIG. 1, apparatus 11 includes a digital image analysis and processing system 13, which is broadly shown in FIG. 2. Apparatus 11 includes a high-resolution microscope 15 for viewing magnified specimens on a support or stage which may include a glass slide 14. Microscope 15 has an adjustment or positioning means 70 for focusing optics, such as a condensing lens, on slide 14, and further includes a platform 51 incrementally movable in the X and Y directions through positioning means 12 and 17, respectively, to view the total area of slide 14. Positioning means 12, 17 and 70 may be mechanical adjustment verniers for microscopes.

The specimens, which may be cells mounted on the slide, are in the field of view of the magnifying microscope, and are viewable or reviewable through an imaging system 13 with image acquisition apparatus 18 as well as being visible for analysis in the viewing optics or ocular lens 24. Apparatus 18 is operable to receive the light image at the intensity projected from the specimen field of view. Apparatus 18 thereafter converts the single light beam image into two analog signals [red, blue], which can be individually monitored, sampled and digitally processed by image analysis system 13. Image analysis system 13 is controlled by a system control 22 in the form of a digital processor, such as a personal computer.

An operator, such as a pathologist or laboratory technician, interactively communicates with system control 22 through a keyboard 36. The operator interacts with the system to quantitate nuclear DNA, as well as classify cell objects, by review of two displays or monitors 37 and 62. Image monitor 37, which is the first display, is a conventional RG beam video monitor providing a display through system control 22 and image acquisition apparatus 18, which is the same image provided through a field of view by ocular lens 24. The second display is provided through instruction monitor 62, which is a second conventional RG beam video monitor providing the operator with interactive prompts, images, information and instructions from a system program executed by system control 22.

Keyboard 36 is illustrated as a conventional AT type keyboard having the following: a plurality of function keys F1-F10; a plurality of alphanumeric keys including special function keys such as ENTER, SHIFT, CONTROL and ALTERNATE; and, cursor control keys including an up/down left/right arrow key, a numeric keypad, a numeric lock key and an escape key.

Keyboard interface 35 translates the keystrokes of the operator into numeric codes for system control 22. Printer 38 is provided to reproduce reliable hard copy output of statistical data and reports generated through apparatus 11.

Image analysis and processing system 13 is illustrated in FIG. 2, which is a functional schematic of apparatus 11. Processing system 13 can analyze a plurality of specimen cell objects or components from the image in the field of view provided through microscope 15 of the plurality of cells on slide or support 14. The image provided through microscope 15 includes light communicated from a variable or fixed intensity source 19 transmitted through slide 14 and thereafter resolved through microscope optic or objective lens 16. As shown in FIG. 1, microscope 15 is a compound microscope with objective lens 16 and ocular lens 24, which may be adjusted by means known in the art.

Light source 19 transmits light of a relatively broad band spectrum in the visible range or band of light through the cell objects or plurality of cells on slide 14. The optical density of the image converts the light from source 14 into a different intensity output beam communicated to objective lens 16, which differential intensity is dependent upon the percentage of light transmission or, conversely, the percentage of light absorption by the cell object. The visible indication of this phenomenon is presented by the areas of slide 14 wherein no cell objects exist, and therefore these areas will transmit light of high intensity [transparent], whereas areas having nontransmissive or less transmissive objects will appear darker. Generally, an unmodified cell or cell object is relatively transparent and the features of these cells or cell objects are almost indistinguishable. Therefore, the practice of staining cell objects optically enhances the features or objects within the individual cells to highlight or darken them over surrounding features and/or background. In the present invention the stains may be bound to the particular cell by any mechanism, such as absorption, adsorption, ionic bonding, covalent bonding or other method.

The image from each of the cells or cell objects on slide 14 is projected or transmitted to image acquisition apparatus 18 through an optical image splitter 25. Splitter 25 partially reflects the transmitted image to the image acquisition apparatus 18 or the other detector, such as ocular lens 24. Splitter 25 communicates approximately, as a preferred embodiment, 90% transmission of the transmitted light from slide 14 to image acquisition apparatus 18 for subsequent conversion to the optical image for the two scanned electronic signals [e.g., red, blue] through a point-by-point electronic analysis, which represents a monochromatic image of the optical intensity of each of these points in the image communicated to splitter 25, that is, a true color image of the field provided to the analyst at viewing optics 24.

Figure 3:
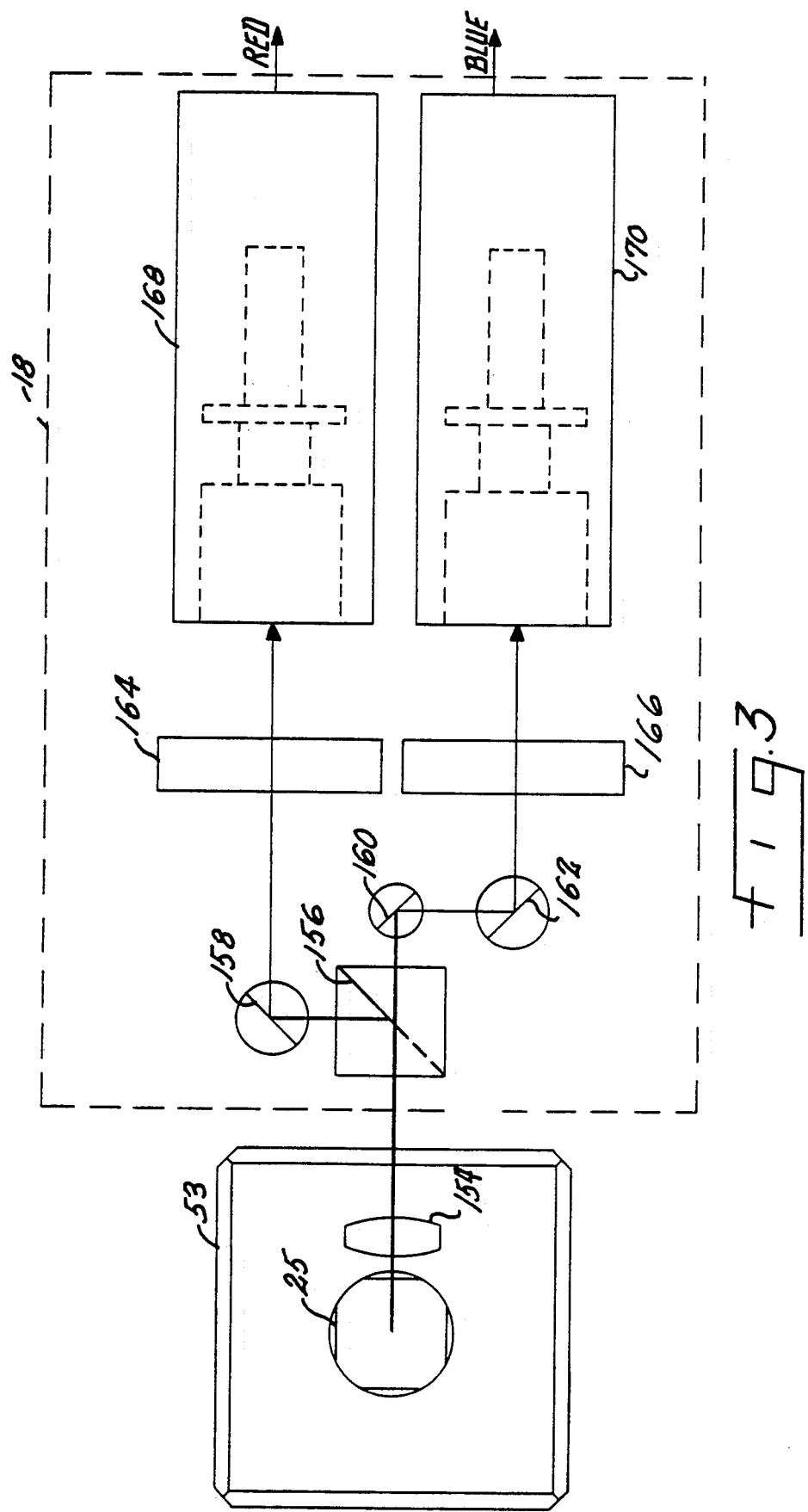
FIG. 3 is a schematic block diagram of the image acquisition apparatus of FIG. 2.

FIG. 3 illustrates an embodiment of the several elements of image acquisition apparatus 18, which includes reflecting mirrors, an image splitter, filters and video cameras, including a digitizing network. As noted above, the light from variable wavelength source 19 is transmitted through slide 14 with a cell or plurality of cells thereon and communicates an image to beam splitter 25, which is mounted in a holder 53. A first true color image is communicated from beam splitter 25 to the viewing optics or ocular lens 24 for focusing and manual review thereof. In addition, a second true color image is transmitted by beam splitter 25 perpendicular to the vertical path from slide 14 to a focusing lens 154 and image acquisition apparatus 18. Lens 154 provides a focused image, that is, a real image, to the image acquisition apparatus 18.

Image acquisition apparatus 18 includes: a plurality of optical elements including a second beam or image splitter 156; reflecting mirrors 158, 160, and 162; and, two monochromatic optical filters 164 and 166. Image acquisition apparatus 18 also includes first video camera 168 and second video camera 170, which receive separate portions of the projected image from second image splitter or beam splitter 156.

The projected image-carrying beam from objective lens 16 and first beam splitter 25 is communicated to both the microscope optics or ocular lenses 24 and to second beam splitter 156. In a preferred embodiment, second beam splitter 156 communicates approximately all of the light above a predetermined wavelength for reflection by mirror 158 through optical filter 164 to first camera 168. Similarly, the light beam wavelengths below the predetermined wavelength are communicated to reflecting mirrors 160 and 162 for reflection through second filter 166 to second camera 170. Filters 164 and 166 are narrow bandpass filters, which filter the light beams transmitted therethrough to substantially provide a light frequency at a specific wavelength. Filters 164 and 166 operate within narrow specified limits and provide an optical block to wavelengths outside this narrow band of wavelengths. Thus, the light beams provided to first and second cameras 168, 170 are essentially monochromatic images of the field of view on slide 14. Filters 164 and 166 may be changed and selected for either color or wavelength operability, and thus second filter 166, for example, may be a blue filter with a narrow bandwidth different than the width of filter 164. That is, first filter 164 may operate at a wavelength such as $620 \pm 10$ nanometers, and second filter 166 may operate as a blue filter with wavelengths near $500 \pm 10$ nanometers.

Each video camera or sensor 168, 170 is operable to convert the monochromatic, optical, light-carried image of slide 14 on a point-by-point, that is, digital, field into a scanned electronic signal representing the optical intensity or density of each point pixel, in this light image. The output of the first and second cameras 168, 170, which is formatted as a standard NTSC analog video signal, is communicated to an analog or digital converter of a pair of image processing interfaces 21, 23 (cf. FIG. 2), for conversion to a digitized signal, which is received and stored by system control 22. As the image under review on slide 14 is continuously scanned, a real-time image of the area under review is provided by image display 37. In the above-noted Feulgen stain example, dual camera arrangement 168, 170 provides a red color image and blue color image, respectively, simultaneously to the control system, which images may be mixed to provide a combined or focused image of the field of study. Each monochromatic digital image is stored as a $512 \times 512$ array of pixels, where each pixel has a measured light intensity of 0 to 255 [8 bits].

The parfocal arrangement on either side of first image splitter 25 allows the same or similar image to be reviewed through the ocular lens 24 or on image display 37. The platform 51 may be positioned by the manual X, Y adjustment positioning means 12 and 17 as the operator views a field or reviews a slide to provide a field of interest thereon. Thereafter, the computer-enhanced, digitized image of the selected field is displayed on image display 37 for further analysis. An X-position sensor 26 and Y-position sensor 27, shown in FIG. 2, generate location or position signals to position interface 34 on lines 26a and 27a, respectively, which digitizes these signals to provide apparatus 11 with an accurate coordinate representation of the field of study. Thereafter, the field under review may be reselected at a later date for additional study without scanning the total slide in anticipation of possibly locating the same or similar field of view.

Displays 37 and 62 are controlled by system control 22 through standard video monitor interface circuitry 39 and 61, respectively. Similarly, keyboard 36 and printer 38 communicate with system control 22 through conventional interface circuits 35, 41, respectively. System control 22 controls a random access memory and other bulk memory storage devices in the form of either floppy and hard disk arrangements or drives 75 through a memory control interface 71.

Interface circuits 21, 23, 34, 35, 39, 41, 61 and 71 can be selectively provided on a printed circuit board or boards mounted in the back plane or card connector of a conventional personal computer integral with or forming system control 22. For example, the personal computer can be one manufactured by IBM corporation with a model designation AT, or a similar model compatible therewith. This control system 22 can be operated under a disk operating system such as PC DOS, Version 3.1 or later-issued programming. The system software for the image analysis may be provided on any storage and/or operating means, such as disk drive 75, or a hard disk, and could thus be introduced into the computer operating system by a means such as a floppy disk 77. The system software would be read from disk 77 and loaded into ram 73. Thereafter, the program control would be transferred to system software from the operating system to regulate the various hardware elements of apparatus 11, which were previously set.

Image analysis system 13 provides an interactive program control which projects a number of instruction screens or images on instruction monitor 62 to assist the operator in the quantitation of nuclear DNA found in one or several cells or subpopulations displayed on image monitor 37. Interactive responses by the operator and the menu selections for the different instruction screens will thus function to perform the image analysis of the projected image on monitor 37.

Figure 4:
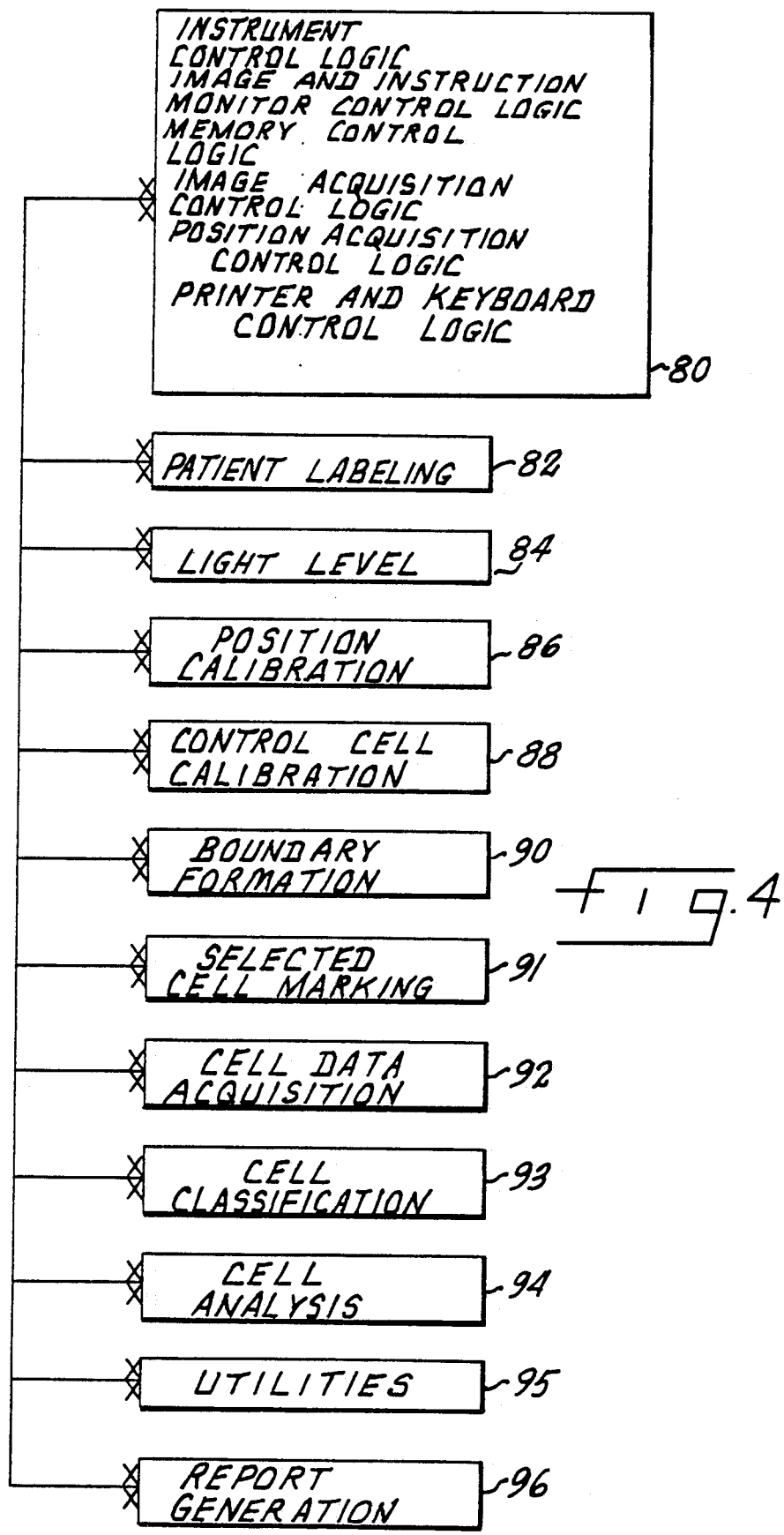
FIG. 4 is a functional system diagram illustrating the major operations of the system control of FIG. 2.

The system functions are more fully illustrated in FIG. 4, where software control logic functions for the hardware of block 80 communicate with software analysis and measuring functions of the system software of blocks 82–96. The software performs an initialization operation, an interfacing of the operating system function, and overall control of the apparatus by instrument control logic. An image and instruction monitor control logic performs screen handler operations for the instruction screens and digital display of digital images of the specimen for both monitors 37 and 62. Memory and disk storage functions are operated or controlled by the software and memory control logic. Input and output for the interactive responses, as well as report generation, are handled by the keyboard and printer control logic. Data from cameras 168 and 170 as well as position sensors 26 and 27, are handled by image acquisition control logic and position acquisition control logic, respectively.

The control logic of the software forms an operating shell, which is utilized by the analysis and measuring functions of blocks 82–86 to control the hardware of apparatus 11 for performing a particular function. This system provides the following: a patient or cell labeling function 82 to identify the particular tissue samples under study; light calibration and position calibration functions 84 and 86, respectively, which are utilized to provide an accurate reference optical density for a particular field and location of such field with respect to a coordinate origin; control cell calibration 88 operating to provide a datum or reference for the various background stains, DNA index calibration, or other function; a boundary formation 90, allowing the operator to select a reference level for the gray scale value for comparison of either the red or blue image; a selected cell marking function providing marking of the cells identified by cytoplasm optical enhancement in the acquired data function; cell data function 92 for storing of gray scale value of the specimen image measurement; cell classification function 93 operable for the operator to classify the acquired cells, and cell analysis function 94 providing different statistical analyses of categorized data; a utility function 95 providing the needed auxiliary type program for assisting in primary function of image analysis; and, a report generation function 96 to provide hard copy production of the analyzed and compiled data from the system onto or by printer 38.

Figure 5:
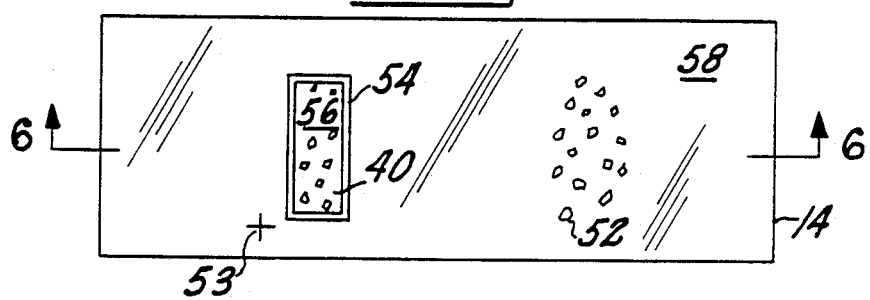
FIGS. 5 and 6 are top perspective and cross-sectional views, respectively, of a microscope slide particularly adapted for use in the image analysis system illustrated in FIG. 1, and having separate areas for calibration cell objects and specimen cell objects.
Figure 6:
Figure 1A:
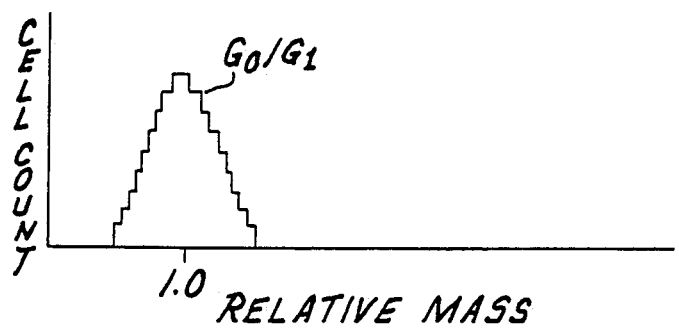
Figure 1B:
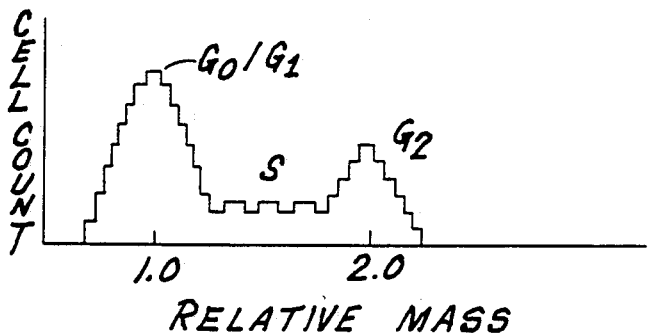
Figure 1C:
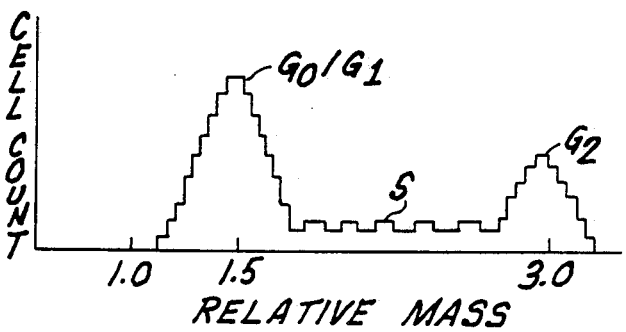
Figure 1D:
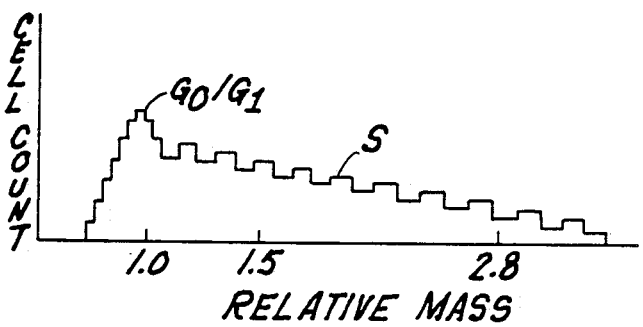

The specimen support is preferably a transparent glass slide 14, as illustrated in FIGS. 5 and 6, which slides come in standardized sizes, such as 1 in. $\times$ 3 in. dimensions. In the present instance, slide 14 may be provided with or partitioned into two sections, with a first control section 56 having control cell objects 40, and a second section or specimen section 58 for receiving the cell specimen 52, which may be analyzed and measured for DNA content or other constituent. Slide 14 may include a border 54 around the control section 56 for rapid identification thereof, and at some convenient location of slide 14, an identifying mark 53, shown as a cross in FIG. 4, may be utilized as a landmark or coordinate origin for the slide field.

Apparatus 11 may be utilized in various offices by persons of varying degrees of skill for image analysis. Microscope light source 19 may be adjusted by different operators to vary the light intensity and in addition, the very nature of the lamp may vary from machine to machine as well as depend upon the age of such lamp. Therefore, it is necessary to provide a calibration function for the light intensity to eliminate or minimize errors, or to accommodate the variation in such light intensity. In addition, the staining rate or the quantity of stain utilized may cause a variation in the staining factor, which may be a function of the utilized volume of the particular stain. Such variation in stain levels causes a variation in the gray level output viewed through microscope 15 by cameras 168 and 170, which gray level is utilized to analyze the particular components, such as DNA content. Consequently, apparatus 11 must be calibrated to eliminate the variable differences to provide a true indication of the actual component amount.

STAINING

The cell staining techniques may be broadly classified in at least three categories:

(1) immunohistochemical staining, which may be based on monoclonal antibody attraction or reaction;

(2) strong chemical binding, such as Feulgen staining, and characterized by high stain affinity and/or covalent binding, which may be indicated by the acid hydrolysis of DNA; and, (3) Ionic staining associated with strong coulombic forces and electrostatic interaction, which may be indicated by a dye-tissue reaction.

Examples of the above type-one staining may be red chromogen or enzymatic alkaline phosphatase or diaminobenzidene alkaline peroxidase. In type two, the Thionin for the Feulgen staining technique for nuclear DNA is exemplary of the strong chemical binding technique. Finally, the type three staining means is exemplified by ethyl green stain, hematoxylin, methyl blue or eosin. An oncogene type of stain may have the characteristics of types one and two above, or it may also be represented by types one and three. The clear-cut or clearly discernible characterization is not as obvious in this case.

The sources of staining affinity noted above are referred to as stain-cell attractive forces. The forces can be illustrated by attractive coulombic forces, Van derWaal force attractions (especially relevant with polarizable materials with large electric dipoles), stain-stain attractions having a complex formation and entropy effects. Other factors affecting staining and staining selectivity include variations in tissue substrate amount; differential stain-cell binding, which can be effected by differential rates of stain penetration into cellular structures; and selective coloration of bound stain. In addition, there are at least the following technical variables affecting staining: structure of the staining reagent; nature of the solvent; presence of co-solutes; temperature; and time. A more expansive discussion of staining and staining mechanisms may be found in "Standardization and Quantitation of Diagnostic Staining in Cytology," edited by M. E. Boon and L. P. Kok.

The calibration material 40 is provided on slide 14 for review by the operator or analyst to establish a calibration or reference position prior to analysis of the unknown cell or specimen 52. As shown in FIG. 5, slide 14 has control cell objects 40 and specimen cell objects 52 positioned thereon for simultaneous staining of collections of cells. This simultaneous staining of both the calibration material 40 and the cells under analysis 52, permits comparison of these two classes or groups of cells to a predetermined and stored reference light intensity, gray level or optical density, of the control cell objects after staining. If the cell objects are stained either too lightly or too heavily, the difference can be compensated for during the quantitative analysis.

In this exemplary illustrated embodiment, control cells 40 are rat liver cells of a known size, shape and DNA content. The control cell objects may be various other cells with dark centers or nuclei that stain well, such as chicken blood cells or trout cells. Alternatively, cell objects may be artifacts printed on the slide or having a cell shape; or the cell objects may be conventional plastic beads of a predetermined size, which will react with a particular fluorescent or enzyme stain when treated simultaneously with specimen cell objects, such as monoclonal antibodies. The reference cell objects will vary between tests and the present invention is not limited to a particular test or cell object.

In the particular example noted above utilizing the Feulgen staining technique, slide 14 with the control cell objects thereon are stained with a dual staining technique. In this example, an alkaline phosphatase staining technique utilizes a primary antibody reagent, a biotinalated secondary antibody reagent, an Avidin-Biotin, alkaline phosphatase reagent, and a chromogen substrate (preferably fast red). Similarly, the Feulgen staining technique utilizes Thionin reagent solution and a rinse agent. In this method, the slide containing control cells and specimen cells in sections 54, 58, is first stained with the alkaline phosphatase process to optically enhance a specific cytoplasmic antigen.

Figure 7:
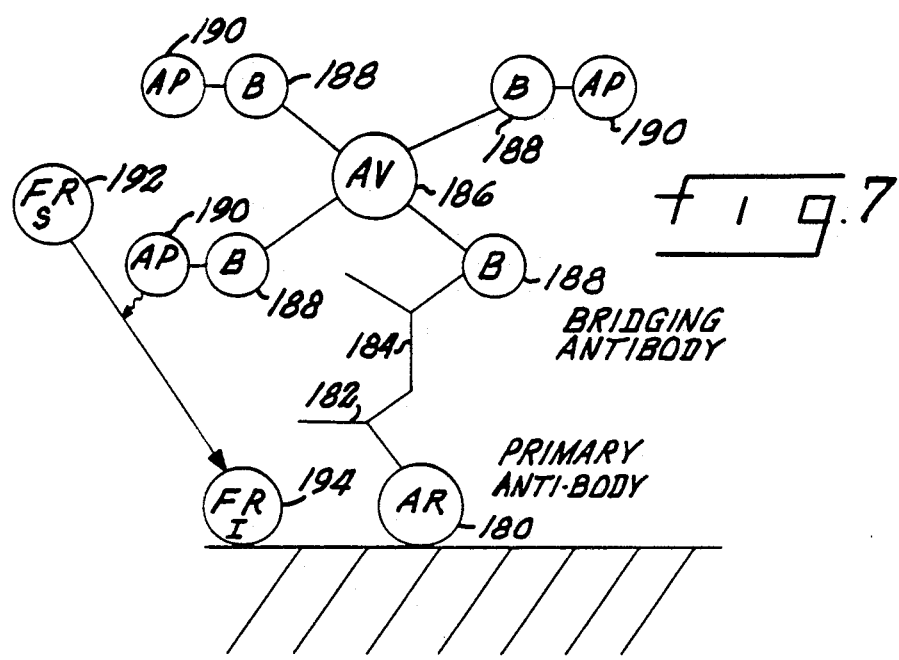
FIG. 7 is a microscopic pictorial view of the binding effects of a monoclonal antibody.

In FIG. 7, the representation of a particular antigen site 180 labeled AR is illustrated as marked and amplified. The site is antigenic against a primary antibody 182 bound thereto. A bridging antibody 184 against the primary antibody is used to bind to the primary antibody, and has affixed a Biotin molecule 188. Avidin-Biotin complex, including an Avidin molecule 186 and three Biotin molecules 188, are added to the bound primary and bridging antibodies. The Biotin molecules 188, are conjugated with molecules of alkaline phosphatase AP enzyme 190. The fourth Biotin molecule site is open for binding the complex to the bridging antibody 184. When a dye, such as fast red molecules 192 in solution, is added to this mixture, the alkaline phosphatase reacts with the dye molecules to produce insoluble fast red molecules 194, which mark the antigen site. While this Avidin-Biotin complex is exemplary, any number of marking techniques and stains may be utilized, as noted below. Alternatively, a bridging or primary antibody, which is anti-alkaline phosphatase, will be utilized and amplified by fast red dye in the previously-described manner.

In the above-noted Feulgen staining alkaline phosphatase methods, the apparatus for the present method provides a dual filtering method to distinguish the areas stained by the red chromogen [cytoplasm] and the areas stained by the blue Thionin [DNA]. These different images, one provided by the red filter and the other by the blue filter, separate the DNA stained area from the cytoplasm area, which contains the specific antigen, and also separates both areas from other cell or field features. The method uses selective filtering both above and below a wavelength through beam splitter 156, and thereafter filtering these selective wave length images by a color filter technique with a narrow bandpass, which provides maximum utilization of available light intensity and minimizes the light intensity for filtering to each of the separate filter elements 164, 166 to improve their efficiency.

Figure 8:
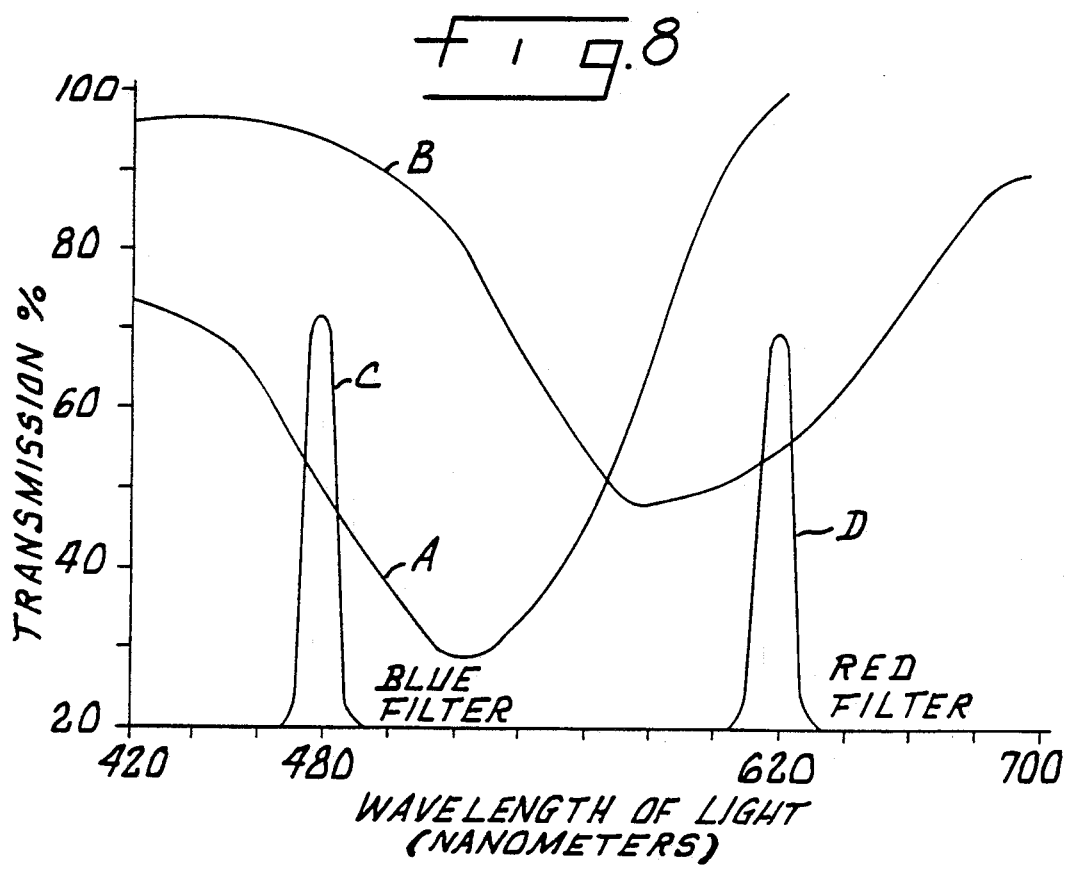
FIG. 8 is a graphical representation of the percentage of light transmission as a function of light wavelength for two stains and the two color filters utilized in accordance with the invention.

Illustrative of the technique is the result shown in FIG. 8, which is a DNA gating technique. The percentage of light transmitted through the nuclei stained with the Thionin dye is noted as Curve A, which is a function of the wavelength of light. The percentage of transmission of the light for the fast red dye is noted as Curve B, which is also a function of the light wavelength. The bandwidth of wavelengths of light passed by the blue filter 166 is illustrated in Band C, and the bandwidth of wavelengths transmitted or passed by red filter 166 is noted as Band D.

It is noted that Curve A, the Thionin dye curve, has approximately its minimal transmission, or is relatively nontransmissive at approximately a 480 nanometer wavelength, while the fast red dye curve, B, is relatively transmissive at this band range. Later work has indicated that for the present invention the analysis should be performed at about 500 nm, which conforms with other analytic techniques noted below. Thus, when the image of the cell population is filtered through blue filter 166, substantially all of the area stained with fast red dye will be essentially transparent and substantially all the area stained with Thionin dye will be visible. Therefore, the areas provided with Feulgen stain can be separated from the cytoplasmic stained areas. Similarly, at approximately the band wavelength around band D of red filter 164, the inverse operation is provided. That is, Thionin curve A is relatively transmissive at this bandwidth, while fast red dye curve B, is relatively nontransmissive. Thus, the cytoplasmic areas containing fast red dye are identifiable and are clearly distinguishable from the DNA nuclear areas with the Feulgen stain.

The above-noted illustration at FIG. 8 indicates that the maximum-minimum relationship of the curves A and B are not precisely overlapping. However, there is a great enough separation between the curves, that is the percentage of transmission difference, to allow the system equipment to provide a clear analytical representation to the monitor for study, analysis and quantification of the cell or cells.

It is apparent that opposite relative differences in the light transmission of the two stains with their reactive components, provide selective areas for filtering. Thus, a convenient and advantageous method for discriminating between these areas with separate staining is provided, and it is recognized that various other staining pairs or conditions may be utilized for different cells and/or cell components to provide similar results for discriminating and distinguishing various cell features.

The system software for DNA analysis in the above example can now determine the mass of cellular DNA through optical density measurement of the specimen cells from the Thionin stain through instrument 11. The mass of the DNA of a stained cell object may generally be obtained from its optical density through the Beer-Lambert law which is well known in the art of microspectrophotometry. This analysis provides the mass distribution of a cell or number of cell objects which are available thereafter for analysis by statistical basis, histogram or other analytical format. The spot size, A, noted for the above Beer-Lambert law, is determined by the number of pixels measured by one of cameras 168, 170. The optical density for each pixel is calibrated by adjusting the light level, focus, and reading a reference optical density for the calibration cells 40 on the slide. This calibration allows conversion of the measured light levels for each pixel into an optical density, a dimensionless quantity. The calibration for the extinction coefficient of the above-noted equation is provided by measuring the optical density for a plurality of control cells 40 to provide a peak for the distribution in relative mass units. As the peak DNA content is known for the control cell distribution, the cells in the field of the unknown specimen can be measured using the relative OD units, and thereafter converting these directly into picograms by comparison to the control cell calibration.

Figure 9:
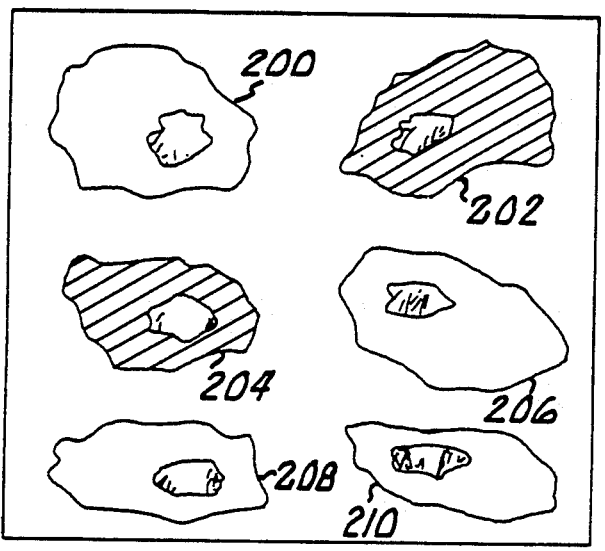
FIGS. 9, 10, and 11 are pictorial representations of images of a cell population illustrating an unfiltered image, a red filtered image and a blue filtered image, respectively.
Figure 10:
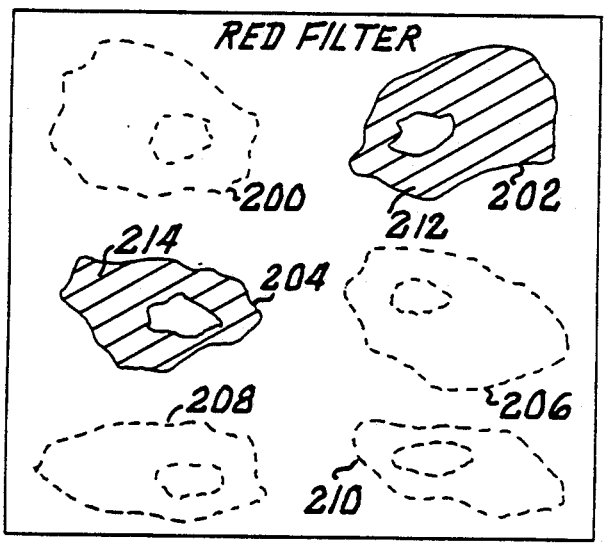
Figure 11:
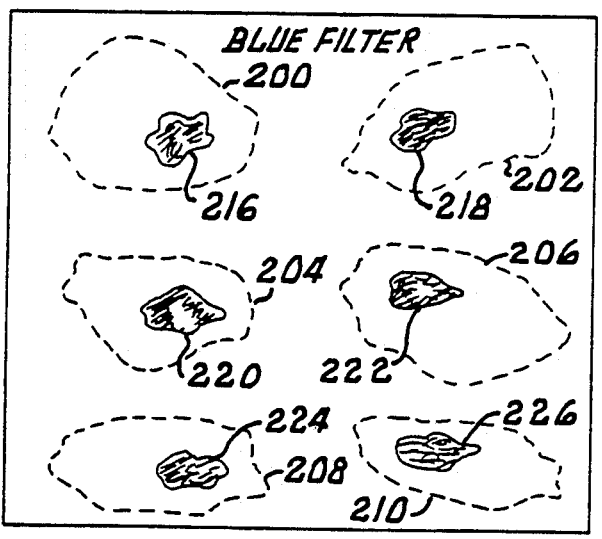
Figure 12:
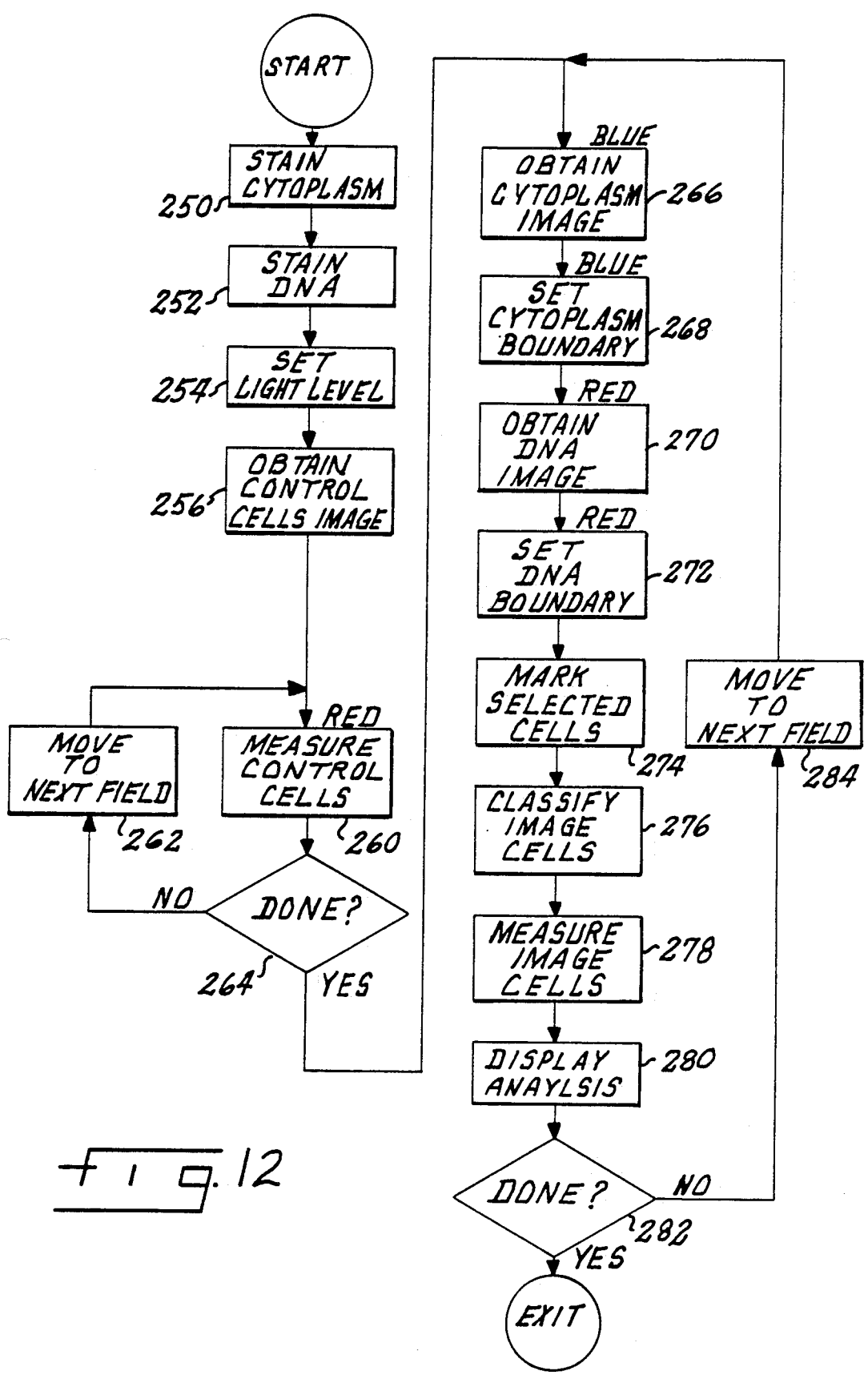
FIG. 12 is a functional flow chart of one preferred method of quantifying DNA for human carcinoma in accordance with the inventions.

FIGS. 9-11 are pictorial representations as follows:
(1) FIG. 9 is the true color image of a field of a slide 14;
(2) FIG. 10 is an image filtered with the red filter; and
(3) FIG. 11 is an image filtered with the blue filter. FIG. 12 is a flow chart of the steps in the method of the present invention to produce quantitation of nuclear DNA.

FIG. 9 illustrates several cells of a subpopulation from one of the fields of microscope slide 14. This subpopulation contains different types, wherein specific cells 202, 204 have been optically enhanced by the alkaline phosphatase staining noted above. All cells 200, 202, 204, 206 and 210 have had the DNA in their nuclei optically enhanced by Feulgen staining with Thionin dye. It is noted that this technique is exemplary and not a limitation. The light beam carrying the image from beam splitter 156 is projected through red filter 164. The image is provided in FIG. 10 and illustrates that only those areas containing fast red dye are visible. These are the cytoplasmic areas 212, 214 of cells 202, 204, respectively, which have been optically enhanced by the staining techniques as they contain a specific antigen that combines with the monoclonal antibody of the alkaline phosphatase stain technique. Cells 202, 204 are different than cells 200, 206, 208 and 210, which are not visible in this image. Further, the nuclei of all cells 200, 202, 204, 206, 208 and 210 are not distinguished or visible in the background, as the optical separation of the Thionin dye and the fast red dye render them essentially transparent.

Conversely, FIG. 11 illustrates the result of projecting the image from beam splitter 156 through blue filter 166, wherein all the nuclei of the several cells, e.g., 216, 226, from the cell population are visible. In this image, the blue filter provides an exclusion of the stained cytoplasmic areas, which are not nuclear stained, and are thus optically different, although stained, and thus transparent.

Figure 13:
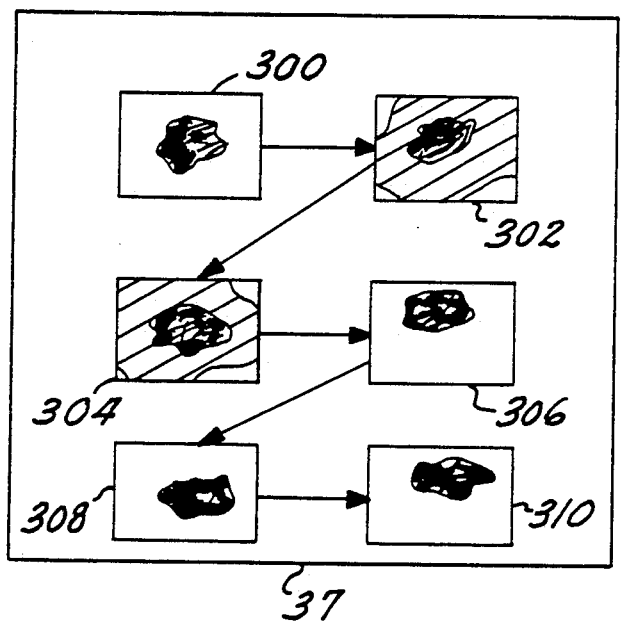
FIG. 13 is a pictorial representation of the image monitor display during the selection process and illustrating the marked cells.
Figure 14:
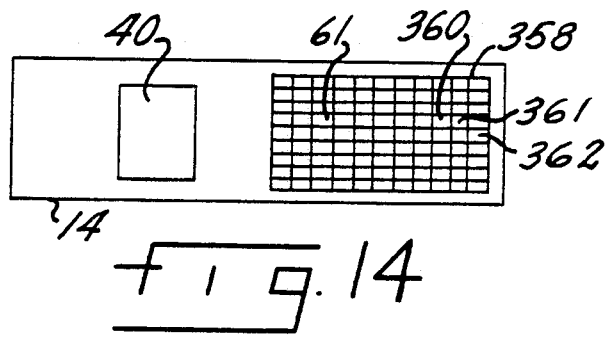
FIG. 14 is a pictorial representation of the multiple optical fields on the slide illustrated in FIGS. 5 and 6.

The areas stained above the threshold set for each filtered image can then be combined by digital overlayment of the DNA image upon the cytoplasmic image, which presents a clear image of the DNA nuclear areas to monitor for typing and analysis where certain cells 302, 304 are marked as to type by an identifying cytoplasmic ring or crescent on the nucleus in FIG. 13. The DNA analysis then proceeds by interactive classification of each cell in the image displayed in the image monitor 37. Specifically marked cells 302, 304 can be included in any class, excluded from any class, or separately classified. Further, it is evident that different optical enhancements and filterings will give rise to different cell typing and increased sensitivity of the classification process.

The method of measuring and analysis of DNA using the marking technique of the invention is more fully illustrated in FIG. 12. In a first step in block 250, a slide containing control cell objects and specimen cell objects is stained with the above-noted alkaline phosphatase technique utilizing fast red dye. The monoclonal antibody is specific against the cytoplasmic antigen, for example, leukocyte common antigens or Cytokeratins. The next step in the process is to stain the slide 14 with the above-noted Feulgen process, utilizing Thionin dye as noted in labeled block 252. After mounting, slide 14 is placed on platform 51 of instrument 11 and positioned to provide a clear field on image monitor 37. The light level is then set, as provided in step or block 254 of the flow chart.

Platform 51 is adjusted or traversed to control cell 40, or an image of a subpopulation of the control cell or cells appears on monitor 37 [block 256 of FIG. 12]. The image is that of the filtered image [red] showing only Feulgen stained areas. The amount of staining to determine the DNA index therein, for determination of the mass through optical density, is found by measuring the optical density of the control cells [block 260]. Generally, the calibration is repeated to obtain an accurate measurement and assessment of the calibration and the process is repeated merely by iterating through the steps in blocks 260 and 262. In block 262, the platform 51 may be manually adjusted to another location to provide a second field of control cells.

The peak of the optical density units is measured, converted into a DNA index, which index is stored in the computer memory. The DNA of the unknown cell sample is thereafter analyzed from specimen section 58 of slide 14, which has been positioned under the focal lens of the microscope by manual adjustment of platform 51.

A cytoplasmic image of the specimen field may be obtained utilizing the blue filter [block 266] and its boundary [block 268]. Similarly, a DNA image of the specimen field is provided through the red filter [block 270] and its boundary set [block 272]. These filtered images are real-time images of the field and may be constantly updated through image acquisition means 18 of system 11. Apparatus 11 combines the two filtered images [block 274] to mark the selected cells on image monitor 37 while displaying the nuclear DNA area. The analysis program then proceeds to the classification step [block 276]. In the classification mode, the image acquisition and combination [marking] ceases and a static or fixed image is projected on image monitor 37.

The cells in the image on monitor 37 are classified by type through an interactive process with an operator. Each cell is noted by the apparatus and the operator selects a classification for the separate cell using nuclear morphology and cytoplasmic markings of the combined image. Classified cells are then measured for the cell component, such as DNA content, [block 278] and the results of the measurements may be displayed [block 280]. This measurement display can be accommodated in several forms and with statistical analyses of the different classifications or combinations of such classifications.

The measurement step can include more than the cells in a single field simply by iterating through the steps noted in blocks 280–284 in FIG. 12. The operator may manually move platform 51 to another specimen field, and the marking and imaging steps may again be repeated as described above. The accumulated data in the measuring steps for the new cell populations is compiled with that of the previously developed cell population data. The display step noted in the above description can be delayed until a significant or required amount of data is accumulated, or display of each iteration may be provided at the option of the operator. In addition, the operator may elect to bypass setting the cytoplasm boundary and DNA boundary after they have been first set for a specimen image.

Figure 16:
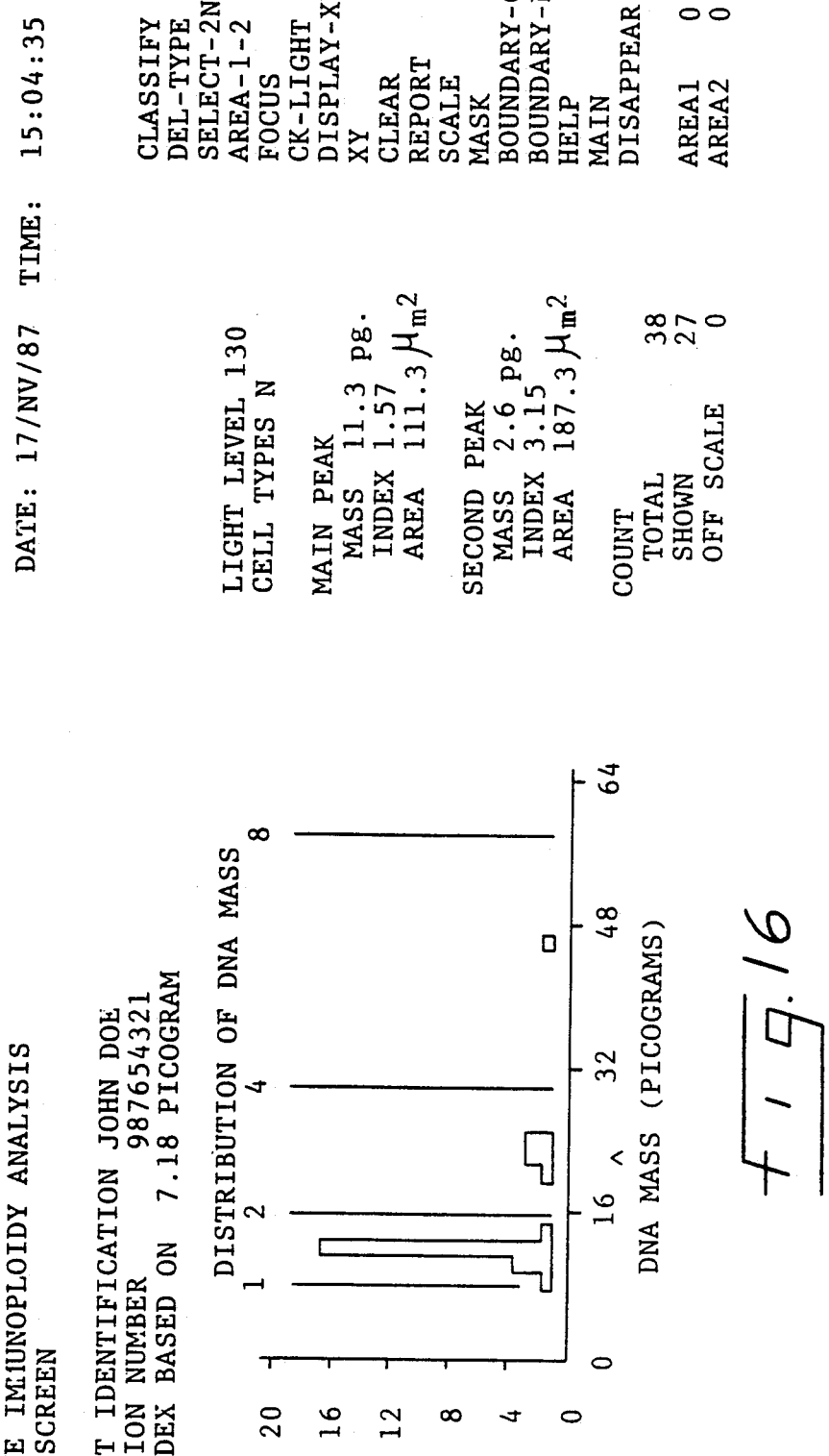
FIG. 16 is a pictorial representation of the analysis screen which appears on the instruction monitor of FIG. 1.
Figure 17:
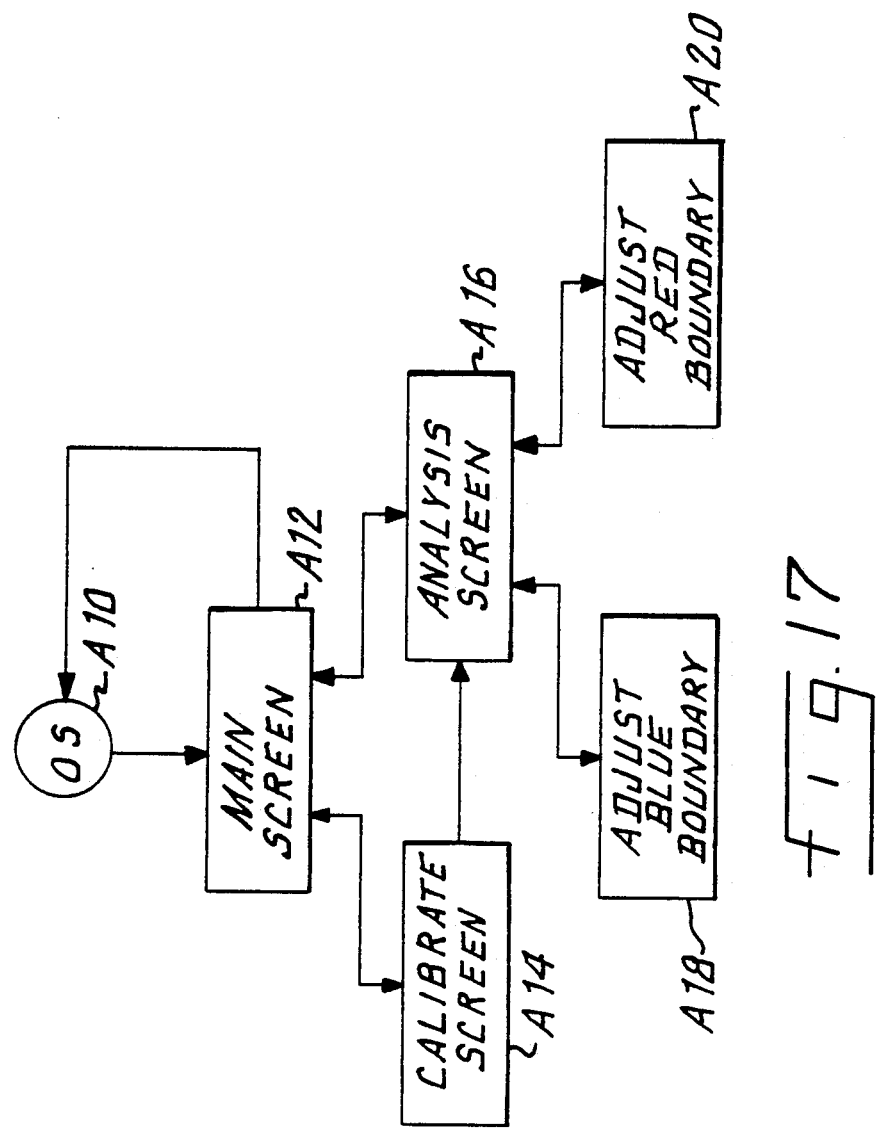
FIG. 17 is a system flow chart of the analysis system screen architecture for image analysis system illustrated in FIG. 1.
Figure 18:
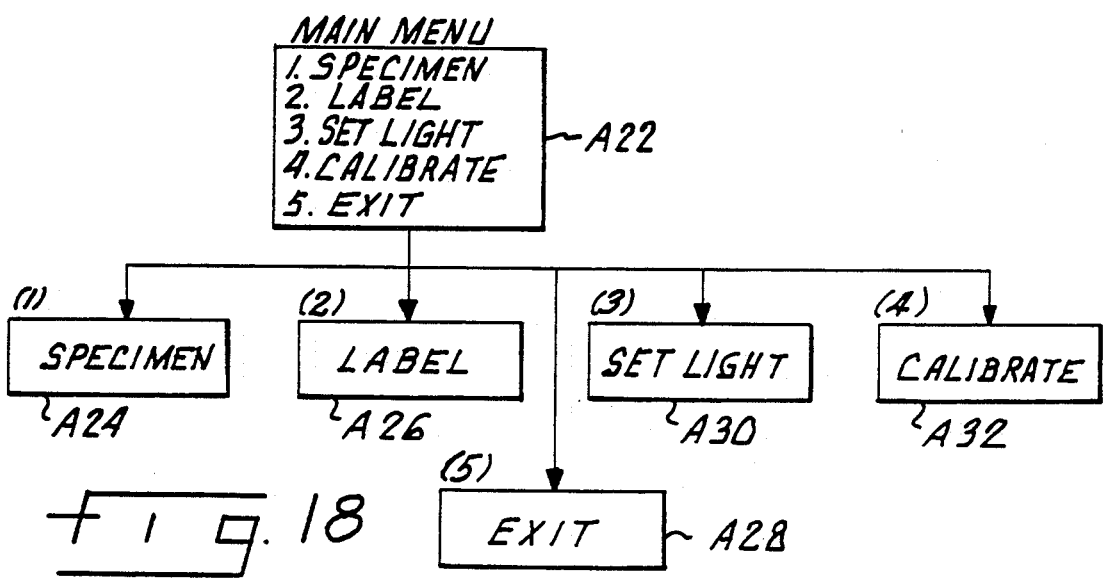
FIG. 18 is a functional flow chart of the main menu of the main screen illustrated in FIG. 17.

FIG. 17 illustrates the screen architecture of the system and the alternative paths that the system takes between screens. Examples of two of the system screens, the calibration screen A14 and analysis screen A16, which appear on instruction monitor 62, are pictorially illustrated in FIGS. 15 and 16, respectively.

In FIG. 17, the system program may be run by an application program of the operating system A10. Selection of the system program from the operating system A10 produces menu A12 on monitor 62. From main screen A12, the operator can select a calibrate screen A14, an analysis screen A16, or exit back to the operating system A10. The apparatus 11 can be calibrated to provide the background or reference-like settings for the measurement in the assay during the display of calibration screen A14 on monitor 62. After completion of the calibration operation, the operator can select the analysis screen A16 from the menu, which subroutine A16 is utilized for measurement and classification of the cell objects of the assay.

Figure 19:
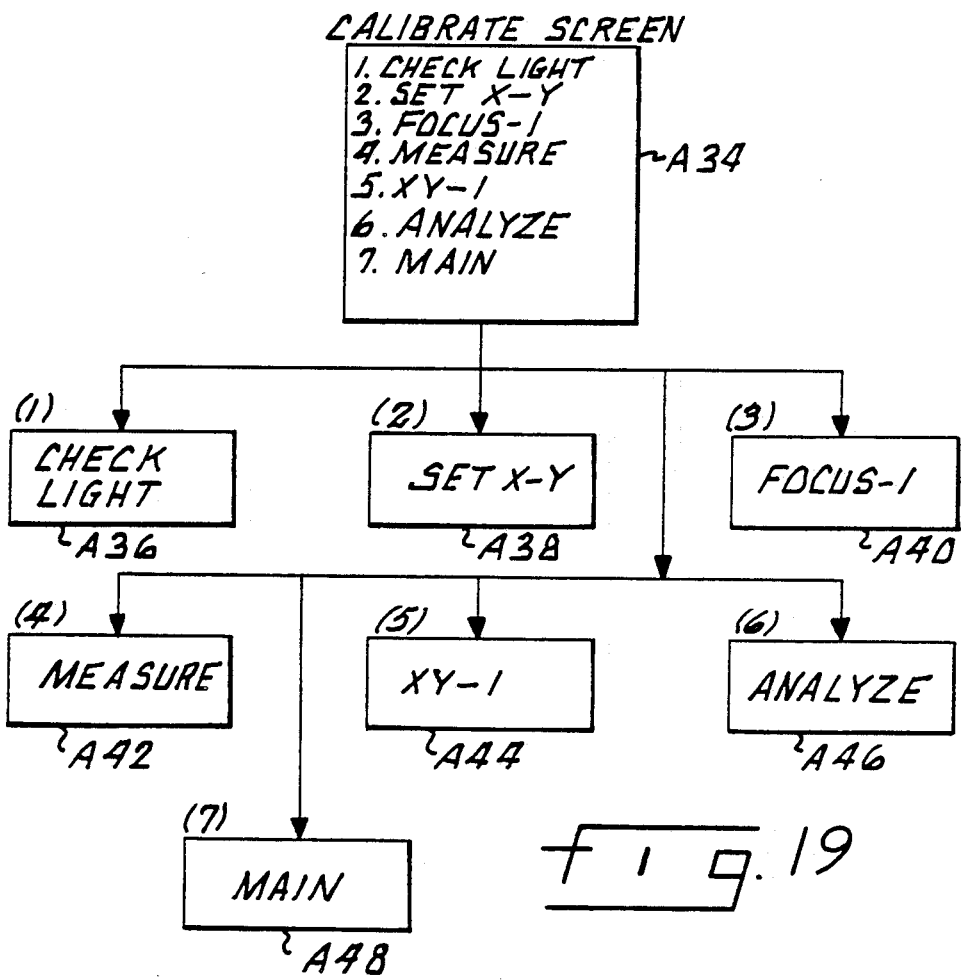
FIG. 19 is a functional flow chart of the calibration menu of the calibration screen of FIG. 17.

The calibration menu, FIG. 19, provides means for setting the current image or field location as the origin, by zeroing a pair of location registers in the software.

The measure function A42, controls the control cell or control object calibration to normalize the staining factor. During control cell calibration, the operator moves the microscope stage by adjustment of the X and Y knobs 12, 17, respectively, to shift cell objects 40 into the field of view on image monitor 37.

Figure 22:
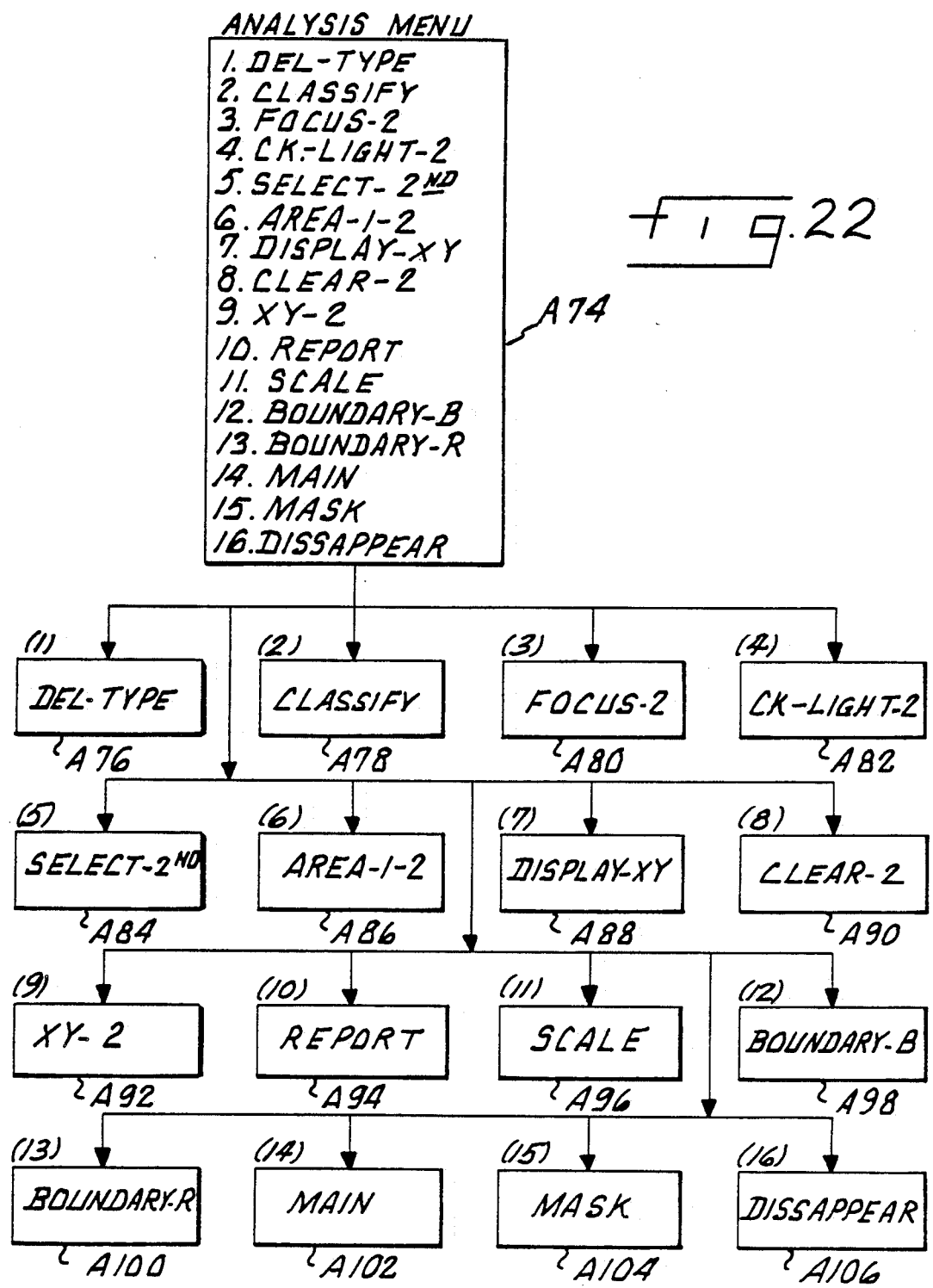
FIG. 22 is a functional flow chart of the analysis menu of the analysis screen illustrated in FIG. 17.

Additional functions are provided on the various screens for various operations of the process. These include: the X-Y function to aid in the positioning of platform 51; the FOCUS-1 function A40 to provide color enhancement to the image; the analyze function, which provides a menu function shown in FIG. 22, to perform the DNA measurements on the cellular material; the check light-2 function A82 calculates the light level of the current image; the select-second function A84 permits the user to select the second peak on the histogram displayed on an analysis screen; the classify function A78 allows the user to classify the cells or objects on image monitor 37; the display X, Y function A88 changes the display from the analysis screen to the X, Y field coordinates screen; the clear-2 function A90 clears all analysis-related areas of data; the focus-2 function A80 provides color enhancement; the area 1-2 function A86 allows the user to specify two areas in the histogram displayed on the analysis screen.

It will be appreciated that the various stained cell calibration steps may be eliminated or combined and performed simultaneously, rather than in the abovedescribed order, sequence and manner.

Optics and Equipment Alignment

In FIG. 3, the image acquisition apparatus 18 encompasses a beam splitter 25 secured and mounted in a holder 53, which holder also secures focusing lens 154. The focused and magnified image provided from the light source 19 and microscope 15 enters beam splitter 25 mounted in holder 53. Beam splitter 25 provides an image for manual observation of the cell under analysis through the viewing optics or ocular lens 24 as well as apparatus 18. In FIG. 3, holder 53 and beam splitter 25 are generally centrally located to project a magnified image light beam along the longitudinal axis of the image acquisition apparatus 18 and has second beam splitter 156 likewise aligned on this longitudinal axis. This FIG. 3 system provides a light path to the cameras which is longer than desirable, as it requires reflecting a light beam of lower intensity than the beam from first beam splitter 25. Consequently, an alternative path is provided, as noted in FIG. 23, to initially reflect the higher intensity polychromatic beam, thereby providing a more uniform beam intensity to both video cameras. That is, second beam splitter 156, which may be a dichroic beam splitter, divides the higher intensity first light beam into two light beams of approximately equivalent intensities. This arrangement provides more closely matched beams at the video cameras, which reduces the adjustments required to balance the overall image system. A further benefit of this structure is a more compact assembly with easily adjustable components in the optical circuit.

Figure 23:
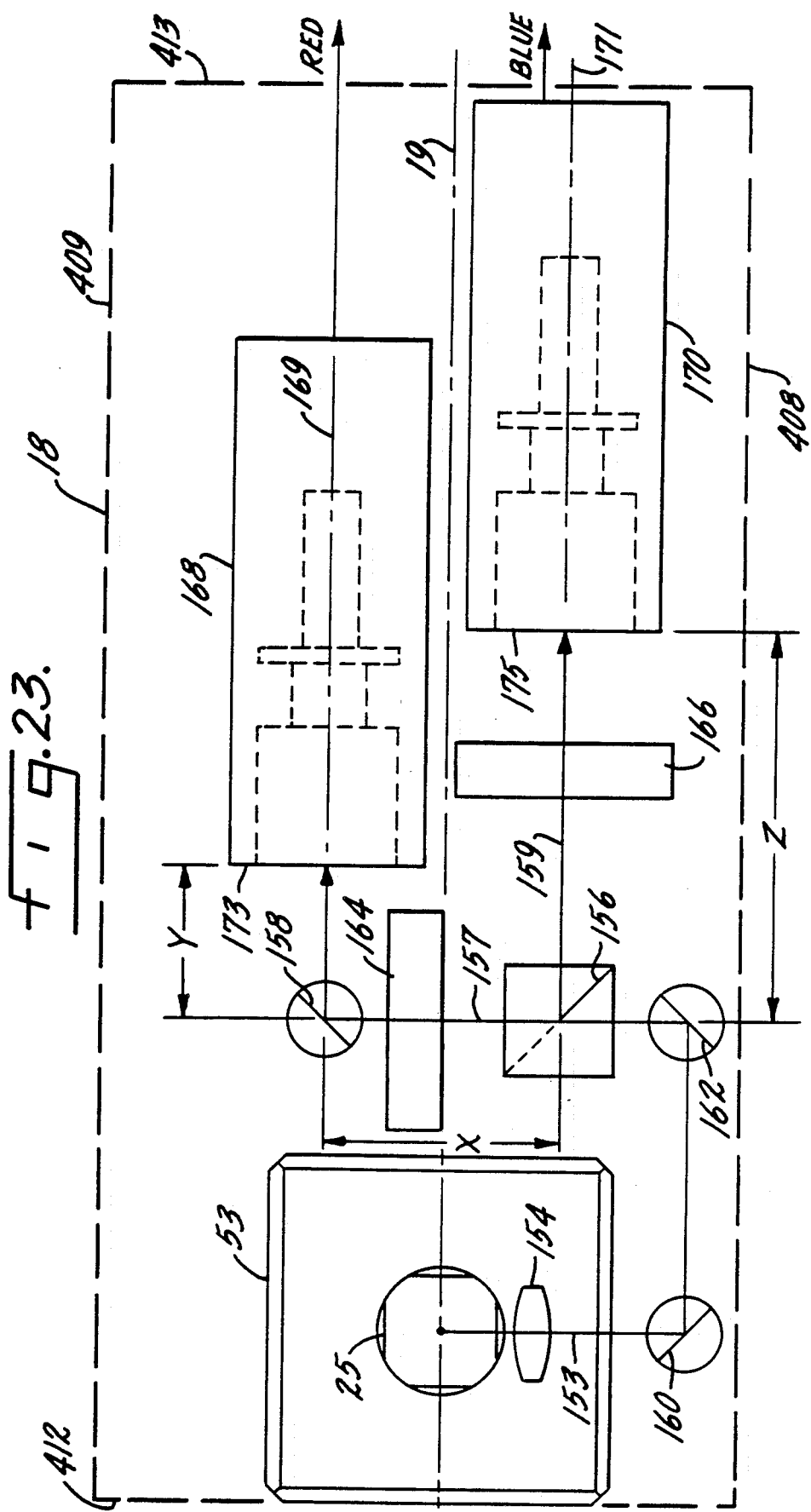
FIG. 23 is a top plan view of a diagrammatic representation of an alternative embodiment of the image acquisition apparatus of FIG. 3.
Figure 24:
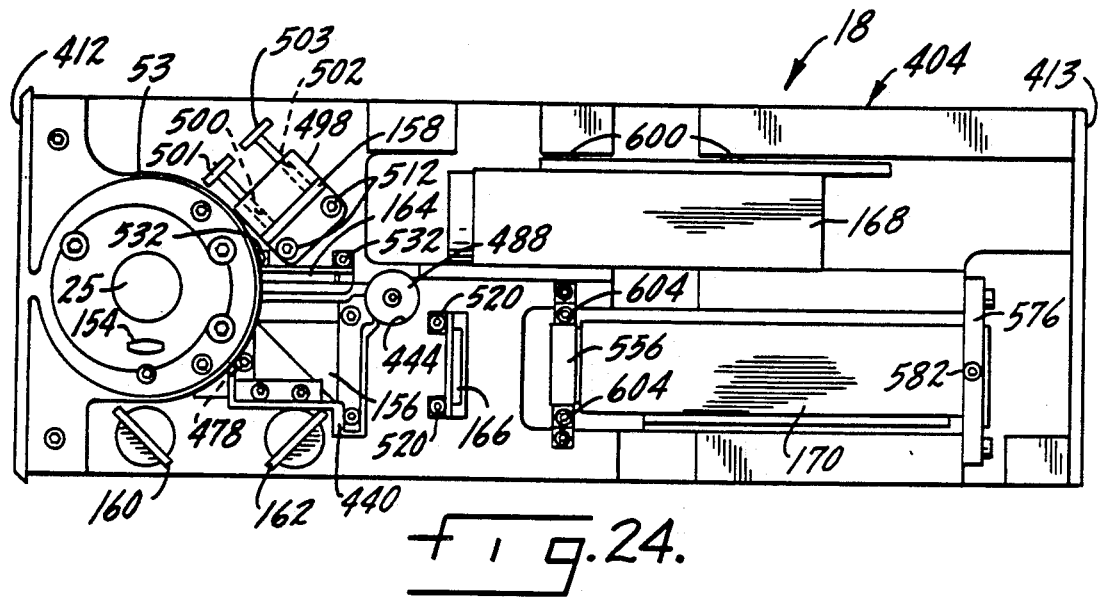
FIG. 24 is a top plan view of a diagrammatic representation of the image acquisition apparatus of FIG. 23.
Figure 25:
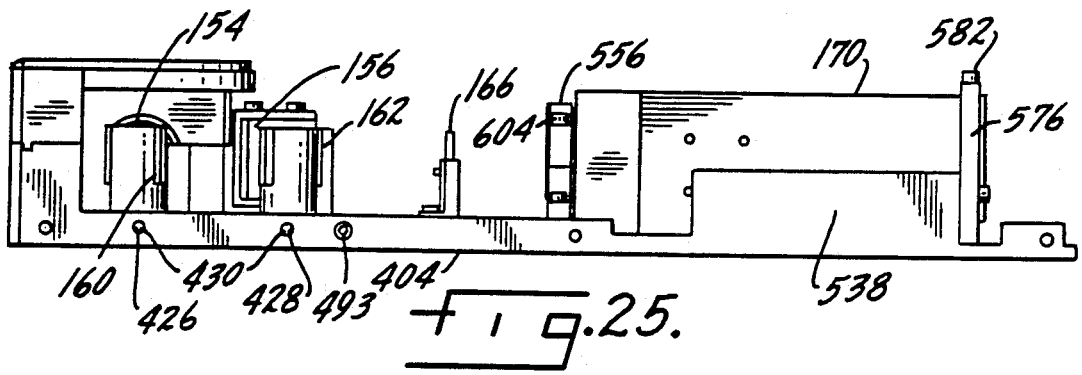
FIG. 25 is a first side plan view of one side of the apparatus illustrated in FIG. 24.
Figure 26:
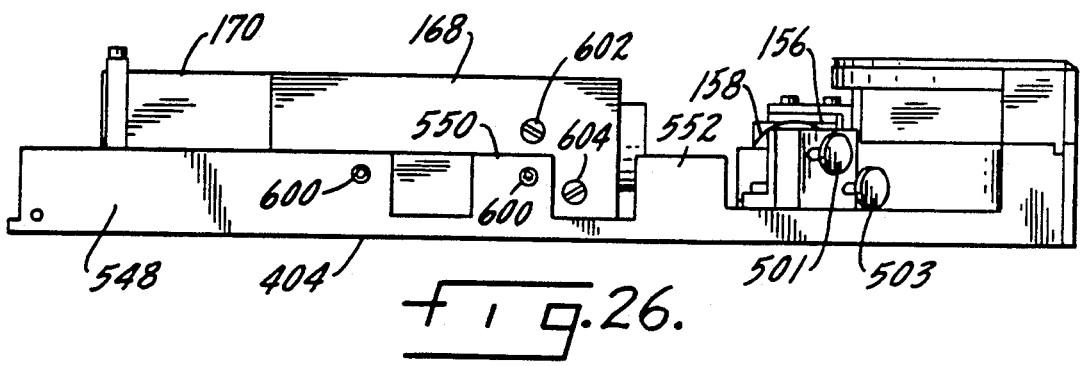
FIG. 26 is a second side plan view of the apparatus illustrated in FIG. 24.

In FIG. 23, image acquisition apparatus 18 is illustrated in a generally rectangular outlined manner with a longitudinal axis 19, which is parallel or generally parallel with the longitudinal axis 169 of first video camera 168 and axis 171 of second video camera 170. In this alternative embodiment, focus lens 154 is positioned in holder 53 at a location perpendicular to longitudinal axis 19 to receive light beam 153 carrying the magnified image from beam splitter 25. This image or light beam 153 is projected through focus lens 154 to first mirror 160, for reflection to second mirror 162 and second beam splitter 156. In this configuration, the image or light beam 153 is projected normal to axis 19, reflected at first mirror 160 at about a right angle to second mirror 162 and again reflected at a right angle for communication of the magnified image to the second beam splitter 156, which second reflection from second mirror 162 is illustrated along a line parallel to the image line of first light beam 153. Thereafter, second beam splitter 156 splits the first light beam 153, which has only suffered attenuation from reflection, into a second light beam 157 and a third light beam 159.

As noted, beam splitter 156 may be a dichroic beam splitter, that is operable to split or divide a first or impinging light beam into a second and third light beams. The second light beam may be transmitted light above a predetermined wavelength and the third light beam may be light reflected below the predetermined wavelength. The order of transmission-reflection through the beam splitter is not limited thereto, but is merely an example. A more expansive development of this phenomena may be acquired by a topical review of light polarization and Nicol prisms in a standard or optic-related physics text. Dichroic filters or beam splitters may be selected to be operable at different predetermined wavelengths.

As an example but not a limitation, light beam 157 is below a predetermined wavelength and is transmitted through first monochromatic optical filter 164 for communication to and reflection from third reflecting mirror 158, which reflects light beam 157 at about a right angle, that is generally parallel to longitudinal axis 19, to first video camera or sensor 168 at the first camera front plane 173. Third light beam 159 is reflected by splitter 156 through second monochromatic light optical filter 166 to second video or sensor camera 170 at its front plane 175. In this configuration it is noted that the light beams are projected or reflected at right angles or generally right angles to the intersecting or reflecting planes such that the beam essentially travels either parallel to or perpendicular to longitudinal axis 19 of the image acquisition apparatus 18. First monochromatic optical filter 16 and second monochromatic optical filter 166 are in proximity to the second image beam splitter 156, which arrangement provides the maximum intensity of the split image light beams and minimizes the potential attenuation suffered by communication of such beams by reflecting or filtering devices.

As noted above, second image beam splitter 156 splits first light beam 153 into a continuous spectrum with a bandwidth below a predetermined wavelength, which is second light beam 157, and another continuous bandwidth spectrum above the predetermined wavelength, which is third light beam 159. These light beams are projected or communicated to first video camera 168 or second video camera 170, respectively. First light beam 157 is provided to first camera 168 at its front plane 173 through first monochromatic optical filter 164 and mirror 158. First filter 164 is specifically chosen to provide an approximately monochromatic optical image at a predetermined wavelength, that is, it filters out wavelengths outside the first predetermined wavelength. Similarly, the second monochromatic optic filter 166 filters or selects a section of a light beam bandwidth at a predetermined wavelength for communication to second video camera 170 at its front plane 175. As the bandwidths of the light beams have been narrowed by second splitter 156, the filters are more efficient in selectively providing the selected wavelength light to cameras 168, 170.

In FIG. 23, the separation distance from second image beam splitter 156 to the third reflecting mirror 158 is noted as X; the distance from the third mirror X to front plane 173 of first video camera 168 is Y; and, the separation from second image beam splitter 156 to the front plane 175 of second video camera 170 is denoted as Z. In this configuration, the sum of the beam path or distances X Y is equal to the distance Z.

The image from the second beam splitter 156 to second camera 170 in this embodiment, is only projected through the second optical filter 166 and thus, the image or rather the intensity losses to the second video camera 170 due to reflection or interference are minimized. In addition, optical filter 164 is in closer proximity to second image beam splitter 156 to enhance the image to first camera 168 by filtering a light beam which is not attenuated by distance or intermediate reflection or diffraction.

Figure 27:
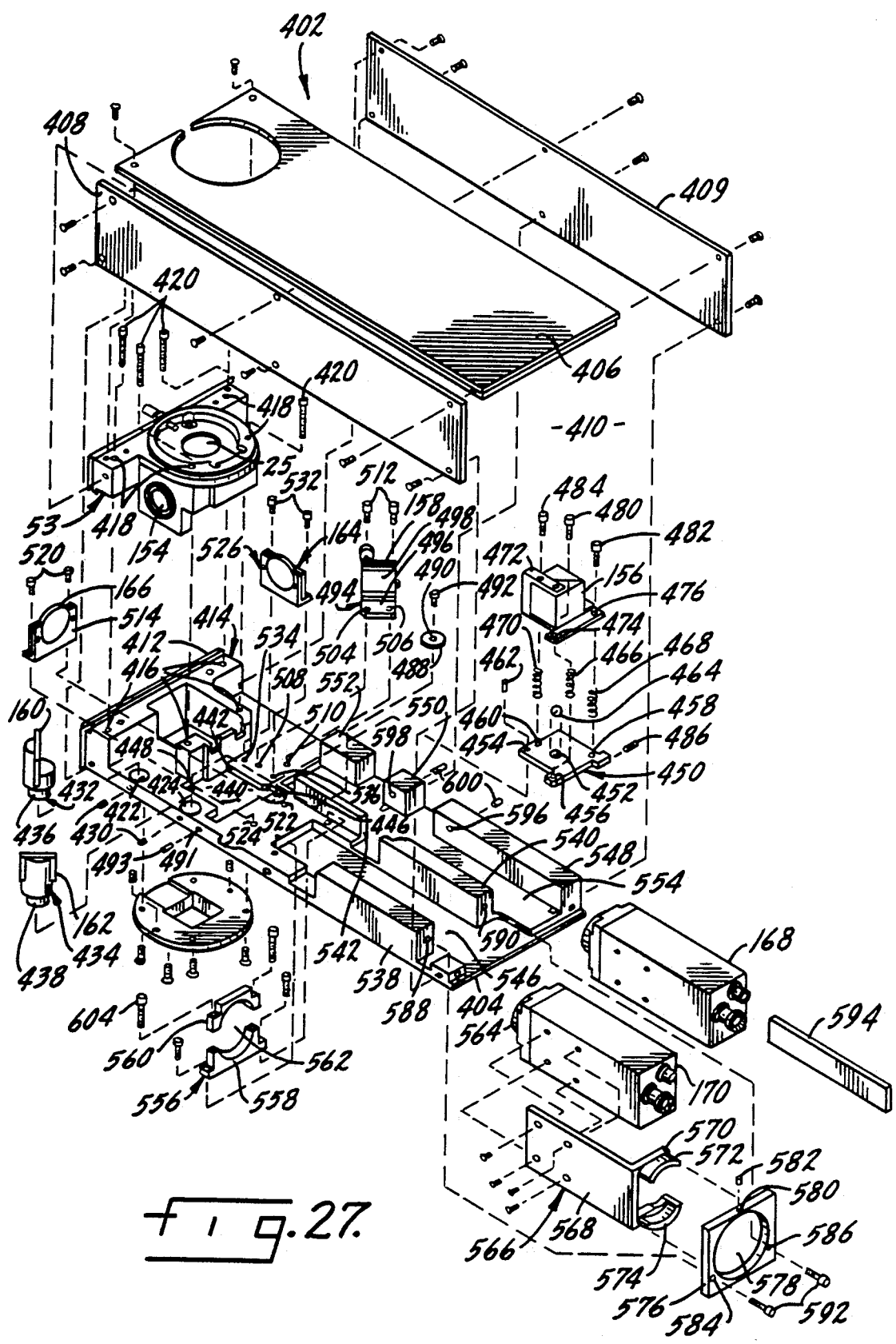
FIG. 27 is an exploded view of the image acquisition apparatus in FIG. 23.
Figure 28:
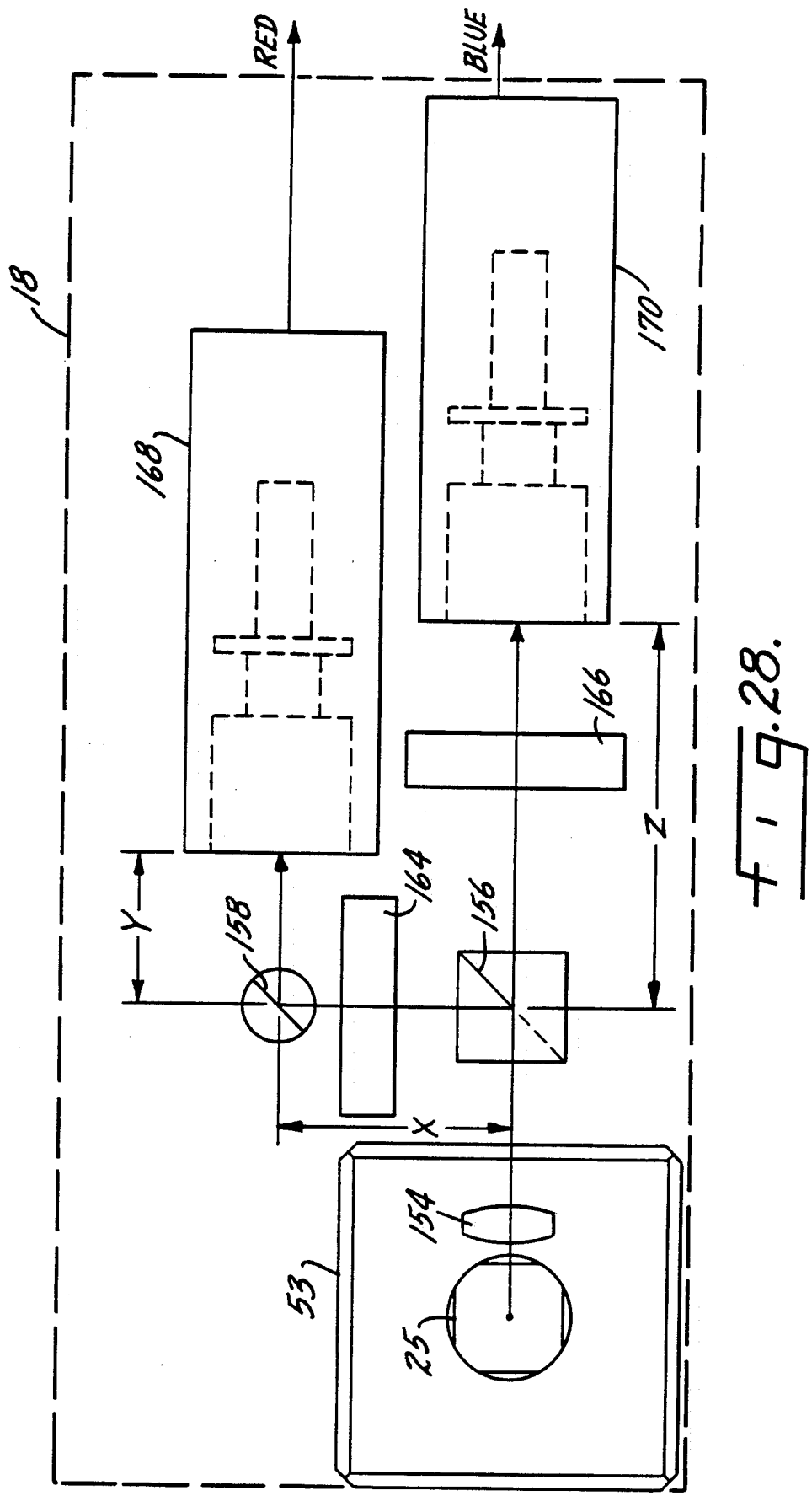
FIG. 28 is a second alternative embodiment of the apparatus shown in FIG. 23.

In this embodiment, which is illustrated in detail in FIGS. 24–27, image acquisition apparatus 18 includes housing 402 which has a bottom panel 404, top panel 406, front panel 412, rear panel 413 and, first and second sidewalls 408, 409. In FIG. 27, which is an exploded view of apparatus 18, housing members 404, 406, 408, 409, 412, and 413 cooperate to define an enclosure or chamber 410 wherein the components of image acquisition apparatus 18 are mounted and operable. Bottom panel 404 is essentially utilized as the mounting base for securing or maintaining the various operating components of image acquisition apparatus 18. In this illustration, bottom panel 404 includes front panel 412 with a base 414 to receive the holder 53 for first beam splitter 25 and focusing lens 154. Mounting base 414 defines a plurality of threaded holes 416 in alignment with through bores 418 of holder 53 to receive securing means 420, shown as threaded screws, which mate with threaded holes 416 to secure holder 53 on bottom panel 404.

Bottom panel 404 includes first pivot socket 422 and second pivot socket 424 as well as first threaded securing port 426 and second threaded port 428 (cf. FIG. 25) communicating with first and second pivot sockets 422 and 424, respectively. First reflecting mirror 160 is mounted on first mounting base 432, which has a first pintle 436. Second mirror 162 is similarly mounted on second mounting base 434 with second pintle 438 affixed thereto. First pintle 436 and second pintle 438 are positioned in first and second pivot sockets 422, 424, respectively, and first and second mirrors 160, 162 are rotatably adjustable in the sockets for positioning the reflection of the magnified image received from focused lens 154. After alignment of mirrors 160, 162, securing means 430 in ports 426 and 428 contact first and second pintles 436 and 438 to secure the mounting bases and mirrors.

Second beam splitter 156 is mounted and operable in a frame 472 on a gimballed base 450. Bottom plate 404 has a recess 440 with a recess sidewall 442 and a washer well 444 (cf., FIG. 24), which well 444 is at least partially open to recess 440. Washer well 444 includes a generally centrally positioned threaded port 446, and bottom panel 404 defines a threaded pivot bore 448 in recess 440. Gimballed base 450 for beam splitter 156 is positioned in recess 440. Base 450 defines a generally centrally located cavity 452 and a gimballed base pivot passage 454 alignable with threaded pivot bore 448. Further, gimballed base 450 has first threaded hole 456, second threaded hole 458, and third threaded hole 460. Threaded pivot and securing pin 462 is operable to extend through pivot passage 454 and mate with threaded pivot 448 to secure gimballed base 450 in recess 440. However, pivot pin 462 also operates as a pivot for the gimballed base when it is not in its secured position. A spherical bearing 464 is positioned in central cavity 452 for slight rotational or rocking movement of the second beam splitter. In addition, a first vertical bias means 466, a second vertical bias means 468, and a third vertical bias means 470 are provided for vertically biasing beam splitter 156. Bottom panel 404 has a threaded locking port 491 communicating to recess 440 to receive a locking screw 493.

Second beam splitter 156 is mounted in mounting frame 472, which frame has first through passage 474, second through passage 476, and third through passage 478 to receive first, second and third frame threaded securing means 480, 482, and 484 respectively. First, second and third passages 474, 476, 478 are alignable with threaded bores 456, 458 and 460, respectively, of gimballed base 450. Mounting frame 472 is positioned on gimballed base 450 with first, second and third vertical bias means 466, 468, and 470 interposed therebetween and aligned with the passages 474, 476, 478 and threaded bores 456, 458 and 460, respectively, of the gimballed base 450. Thereafter, first, second and third threaded securing means 480, 482 and 484 are mated with the threaded bores 456, 458 and 460 through passages 470, 476 and 478, respectively.

Gimballed base 450 with frame 472 and splitter 156 is positioned in recess 440 with pivot and securing means 462 mated with threaded bore 448 through pivot passage 454, whereby gimballed base 450 may nominally pivot about pivot means 462 in recess 440. A lateral biasing means 486, which is positioned in recess 440 between sidewall 442 and gimballed base 450 biases base 450 around pivot pin 462. A washer 488 with a central passage 490 therethrough is positioned in washer well 444 and contacts gimballed base 450 with a segment of its circumference. Thereafter, when the gimballed base is located in a preferred or oriented position, washer 488 is secured by a bolt 492 mating with threaded bore 446 through central passage 490. Threaded pivot and securing means 462 cooperates with securing washer 488 and locking screw 493 to lock or secure second beam splitter 156 in its preferred position against the lateral bias force of bias means 486.

Third mirror 158 is mounted and adjustable on a second gimballed support 494, which has a mounting pedestal 496 and a vertical wall member 498 with third mirror 158 mounted generally parallel thereto. Wall member 498 has a first threaded aperture 500 and a second threaded aperture 502 with first and second threaded adjustment means 501, 503, respectively, therethrough to contact mirror 158. Mounting pedestal or foot member 496 has first and second securing through-ports 504 and 506, which are alignable with bottom plate first threaded bore 508 and second threaded bore 510, respectively. Gimballed support 494 is mounted on bottom plate 404 with a pair of threaded bolts 512 through ports 504 and 506, and mated in threaded bores 508, 510 respectively. Thereafter, mirror 158 is adjusted by rotation of threaded adjustment means 501 and 503.

Second optical filter 166 is mounted in second filter mounting frame 514, which includes second frame first and second through bores 516 and 518. Bottom plate 404 defines a pair of second filter threaded bores 522 and 524, which are alignable with second frame bores (not shown) each receiving one of a pair of securing bolts 520 to secure frame 514 to bottom plate 404. Similarly, first filter 164 is mounted in a first filter mounting frame 526 with a first through bore 528 and a second through bore 530. Bottom plate 404 defines a pair of first filter threaded bores 534 and 536 alignable with first frame through bores (not shown), to receive one of a pair of securing bolts 532 therethrough to secure first mounting frame 526 to bottom plate 404. Mounting frames 514 and 526 are nominally adjustable prior to securing by bolts 520 and 532, respectively.

In FIG. 27, bottom panel 404 includes a family or plurality of upstanding or upright braces extending generally vertically from bottom panel 404 into enclosure 410. More specifically, first upright brace 538 vertically protrudes into chamber 410 along or parallel first sidewall 408 and second upright 540 and third upright 542 are generally centrally located on bottom panel 404 along longitudinal axis 19 and extend into enclosure 410. Uprights 540, 542 are generally centered in enclosure 410 along axis 19. Bottom panel 404 further defines a slot 546 for second video camera 170 between first brace 538 and second and third braces 540, 542. Fourth, fifth and sixth upright braces or brackets 548, 550 and 552 vertically extend from bottom panel 404 into chamber 410 along second sidewall 409. Brackets 548, 550 and 552 are generally parallel to the centrally located second and third uprights, 540, 542, and cooperate with bottom panel 404 and central brackets 540, 542 to define a channel 554 for first video camera 168.

Second video camera 170 is operable and adjustable in slot 546. A front camera mount assembly 556 having a base 558 and a yoke 560 is mounted on bottom plate 404 parallel to and in approximate longitudinal alignment with second filter 166. Camera mount assembly 556 defines a generally spherical or oval shaped port 562 to receive and secure the arcuate and extending lens mount 564 of camera 170. A camera mounting bracket 566 is affixed to a sidewall of first camera 170, such as by a plurality of screws engaging the sidewall and camera 170. Bracket 566 includes a sidewall 568 and an upright extending member 570 perpendicular to sidewall 568, which upright member has an upper arcuate portion 572 and lower arcuate portion 574 extending therefrom. These upper and lower arcuate portions 572, 574 are mountable or positionable in a rear mounting camera support 576 with a portal 578 for securing therein. Rear mounting support 576 has a threaded locking passage 580 for a threaded locking means or screw 582, which locking means or screw 582 contacts one of the upper and lower arcuate portions 572, 574 to secure the location or position of the sidewall 568 and camera 170. Rear support 576 also has two through passages 584 and 586, which are matable or alignable with threaded bores 588 and 590 of uprights 538 and 540, respectively, each open to receive one of a pair of securing means, such as blots 592, to secure camera mounting support 576 and thus camera 170 in slot 546 and chamber 410. In this position, camera 170 is both slightly rotatable and longitudinally movable in slot 546 to focus the camera output or digitizing means for review on screen 37.

First video camera 168 is mounted in and longitudinally movable in channel 554. Camera 168 is slidable along axis 109 in channel 554 to focus the image projected on screen 37, and it may be secured in channel 554 by a pressure plate 594 interposed between the camera and fifth and sixth upright brackets 548 and 550 to secure camera 168 against middle or central brackets 540 and 542 respectively. Pressure plate 594 is secured against the camera 168 by a pair of threaded locking means or bolts 600 extending through passages 596, 598 in fifth and sixth upright brackets 548, 554, respectively. In addition, camera 168 may adjust its signal level with a pedestal adjustment means 602 and an electronic gain adjustment means 604.

After assembly of the above-noted elements of acquisition apparatus 18 on bottom panel 404, first and second cameras 168, 170 are positioned in housing 402 and a magnified image is transmitted to the cameras in their assembled positions by adjustment of mirrors 160, 162 and 158 as well as by adjustment of second beam splitter 156 and the optical filters 164, 166. First and second reflecting mirrors 160, 162 are rotatably adjustable on pintles 436 and 438 in sockets 422 and 424, respectively, to communicate the first light beam 153 from first beam splitter 25 to second beam splitter 156. Second beam splitter 156 is adjustable in recess 440 in a horizontal plane generally defined by bottom plate 404. Gimballed plate 450 may be adjusted by pivotal motion about pivot means 462 against the force of lateral bias means 486. It is recognized that the several securing means utilized to secure the gimbal plate in its desired position are not engaged during the adjustment. The vertical adjustment of second beam splitter 156 is provided by loosening or tightening the securing means 480, 482 and 484 to allow the beam splitter 156 to slightly rock or rotate on spherical bearing 464 against the bias force of vertical biasing means 466, 468 and 470. Finally, third reflecting mirror 158 is adjustable by adjustment means 501 and 503, which provide vertical and horizontal adjustment to generally center the light beam 157 on lens plane 173 of first camera 168. It is further recognized that mounting base 494 may be slightly adjustable initially as the third mirror gimbal assembly is affixed to bottom plate 404. In FIG. 23, the monochromatic optical filters 164 and 166 are placed as closely in proximity to second beam splitter 156 in order to minimize the intensity losses of the light beam signals projected thereto from beam splitter 156. In addition, light beam paths 157, 159 from second beam splitter 156 to first camera 168 and second camera 170, respectively, are approximately equivalent distances, to provide equivalent light intensities to both cameras, which assists in the focusing of the cameras.

Equipment Focusing

The adjusting or focusing procedure for cameras 168, 170 is similar to the procedure for the cameras of earlier models of analysis equipment. A calibration image is provided from microscope 15 through first beam splitter 25 and focusing lens 154 for reflection by first mirror 160 and second mirror 162 to second beams splitter 156. The split beam or beams 157, 159 from splitter 156 are communicated to first video camera 168 and second video camera 170 through first and second optical filters 164, 166, respectively. The first and second image outputs from video cameras 168 and 170 to the digitizing means is projected on screen 37 for review and calibration. Thus, the image in first camera 168 can be individually focused by slidable camera movement along axis 169. Second camera 170 and the image projected therefrom to screen 37 may be focused and adjusted by rotation about or slidable motion along axis 171, which camera 170 is thereafter secured in position. After the camera adjustments, the clamping and support means secure cameras 168, 170. Exemplary of adjustment means are front support 556 and rear or back support 576 wherein securing means 582 may be loosened to allow camera 170 to be rotated about is axis 171.

Apparatus 11 is generally utilized for analyzing biological cell specimens. The image from objective lens 16 of microscope 15, which is the projected and magnified image of the calibration or cell slide, is projected upward to beam splitter 25 to provide the image to both the ocular lens 24 and focal lens 154, which may have a fixed or variable focal length. Magnified image light beam 153 after focusing through lens 154, which is a real and focused image in contrast to an unfocused and virtual image, is reflected by first and second mirrors 160, 162 to the second beam splitting means 156. First beam 153 is divided or split by the second beam splitter 156 into a second light beam 157 and a third light beam 159 with about equal intensity for projection and communication to and through first monochromatic optical filter 164 and second monochromatic optical filter 166.

The apparatus disclosed is particularly useful in the analysis of biological cell structures, although it is not limited thereto. In this biological cell application, cells may be viewed through a compound light microscope; however, only distinct outlines and minimal numbers of cells or cell constituents would be noticeable. The visible cell constituents would only be those that do not require a much greater level of magnification. Therefore, it has been found that the cell structures may be enhanced for optical observation by a chemical technique frequently referred to as staining. The stain reacts, combines or adheres to a specific cell component, thereby outlining or highlighting the component for review and analysis. A Feulgen stain technique was noted and described above. In addition, alternative stains and types of stains were also listed and briefly discussed above.

It is known that cells may be single cell structures but most have at least two components, such as a nuclear DNA with a DNA nucleus and a protein at a protein site associated therewith. Analysis and review of these cells and their various components thus requires selective staining techniques for analysis, for example pathology studies. In some instances, the staining techniques, as noted earlier in the application, provide staining or distinguishing characterization of certain components of the cells, that is, a first cellular component such as a DNA nucleus and a second cellular component such as a protein at a protein site. These are merely exemplary of components of the cells that are available for staining and identification. Among the known proteins are receptors, enzymes, structural proteins, glycoproteins, and lypoproteins. Other potential cell components include nucleic acids (e.g., RNA, mRNA, rRNA, and DNA), hormones (e.g., steroids, estrogen, peptide hormone, and progesterone), and lipids, which are noted as components of the cell membranes. It is appreciated that these are merely representative of cellular components which may be available for staining and identification by an existing or later discovered staining technique. However, in order to observe and identify these various components, and thereafter utilize the gathered information, it is necessary to first present them in an identifiable fashion. Therefore, specific staining techniques are utilized to provide enhanced optical contrasts for combinations of the various components, each component being responsive to a particular stain or staining technique. The following listing provides examples of stain combinations, which are operable to provide contrasting overlapped curves, as in FIG. 8, with graphical plots of transmittance as a function of wavelength where the maximum for at least one plot is adequately separated from the second curve for analysis.

| First Stain Agent | Combining Cell Component | Second Stain Agent | Combined Cell Component |
|---|---|---|---|
| (1) Thionin | Nuclei | Red Chromagen activated by alkali phosphatase | Cytoplasm |
| (2) Methyl-green | Nuclei | Diaminobenzidene (Peroxidase-monoclonal antibody) | Cytoplasm |
| (3) Methyl-green | Nuclei | Red chromagen with alkali phosphatase | Cytoplasm |

The above-noted stains and staining techniques provide enhanced contrast between the various components to be identified and, in addition, have optical characteristics which may be matched or corrected with monochromatic optical filters to provide a discernible and identifiable cell component. In a preferred embodiment, the selected stains react with two separate cellular components to provide a contrasting image at two distinct limited ranges of wavelength or spectral bandwidths. This provides the image acquisition apparatus with the opportunity to segregate each preferred wavelength and to provide the beam splitter and monochromal optical filters the least interference or most narrow bandwidth image signals for resolution of the signals to the selected or desired wavelengths for analysis by one of the video cameras or sensors.

Cells, which have been stained to highlight or characterize and individual cell component, are not as formidable an analytical task as an unstained cell, as the stained component will generally be visibly apparent through a microscope. The optical equipment or optics related to such analysis or recognition are well known. It is recognized that a stained cell exhibits specific optical characteristics, such as transmittance, and more particularly it may have a maximum transmittance at a first wavelength (implying relative transparency) and a minimal transmittance at a second distinct wavelength. In the case where only a single stain is utilized, either of the stained cell components could be analyzed at any wavelength along their curve with some reasonable effort. However, when two stains are simultaneously utilized on a cell to stain or combine with particular cell components, their overlapping spectral emissions may interfere with each other. As a consequence, extensive filtering, both optical and electronic, may be required to discern the specific parameter, characteristic or cell component under investigation. Therefore, it is desirable to provide stains which exhibit contradictory or converse transmission characteristics at approximately the same wavelengths, which in an ideal condition would imply minimum transmittance of a first stain at the maximum transmittance of the second stain, as implied in FIG. 8 at about 500 nanometers. Communication of a narrow band visible light beam through a monochromatic optical filter generally provides a light beam at about a fixed wavelength, which can be selected to correspond to the maximum-minimum point noted above. The image contrast from these two competing stains would provide a more easily analyzed cell component whose stain characteristic is at its minimum transmittance. Similarly, communicating the light beam through a second optical filter (about 600 nanometers in the Example of FIG. 9) would provide a different spread between the spectral transmittance curves.

In the analysis of cells there are different imaging methods, that is different reasons for cell analysis including quantitative immunoploidy (QIP) studies, quantitative nuclear antigen (QNA) analysis and proliferation index. As an example, in an immunoploidy analysis, a type two stain (Feulgen DNA stain) is applied to the nucleus (cf. FIG. 8), and a type one stain of the red-chromagen-alkaline phosphatase variety is applied to outline and distinguish the cytoplasm. At 620 nm in FIG. 8, after acquiring and recombining the separate images, the nucleus of the cytoplasm has approximately 100% transmission and essentially a mask is provided and the nuclear DNA is enhanced for review. In some cases the review is conducted by optical density measurements, which were discussed above, for analysis of the DNA mass. Alternatively, the separation of the curves at approximately 500 nm allows a study of the cytoplasm protein sites, which are distinguished by the greater absorbency of the illustrated red chromagen stain.

Figure 29:
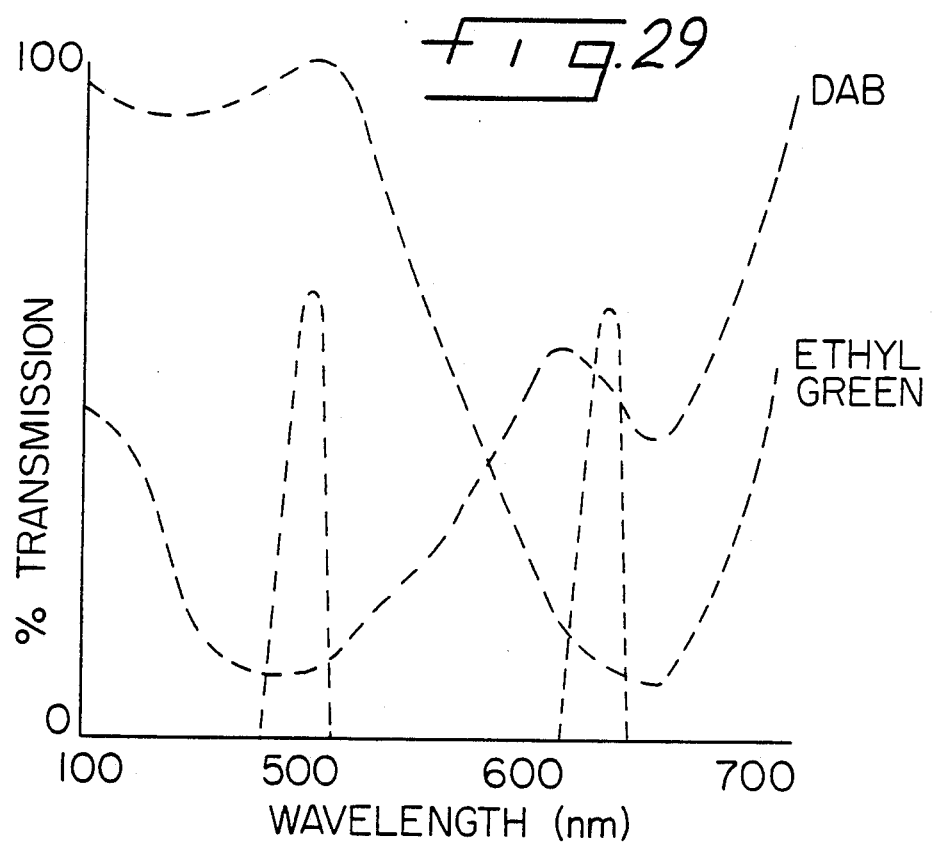
FIG. 29 is a graphical representation of a nuclear antigen measurement spectra.

In the quantitative nuclear antigen measurements, the cell component interest may be restricted to the nucleus and more specifically nucleus components. The components may be nonspecific nuclear proteins and specific proteins. As illustrated in FIG. 29, the nonspecific proteins or all nuclei are stained with a type one (acid-base reaction) stain, such as ethyl green, and the specific proteins or antigens are stained with a type three stain, such as diaminobenzidine (DAB). The immunohistochemical stain (type three) has an antibody stain that is specific to an antigen of some of the nuclei, such as an estrogen receptor, progesterone receptor or a proliferating cell antigen. After application of the peroxidase which colors the antigen, light transmitted through the stained cell will be absorbed or transmitted at different rates as noted in FIG. 29 at the 500 nm and 620 nm ranges. As noted in this Figure, at 500 nm the ethyl green stained nucleus has essentially 100% transmittance, and the DAB stained nuclear component absorbs a large percentage of the light. Therefore, the DAB stained component (red channel) shows through. This method provides a mask for the nuclei and the dark objects are distinguishable. At the second or blue channel, the actual intensity or stain density of the nuclear components is measured, that is, the area of the mask that is immunohistochemically stained. The red channel is thus distinguished, as there is no output from the masked component with 100% transmittance. Earlier analytical color camera developments did not utilize two different stains.

Figure 20:
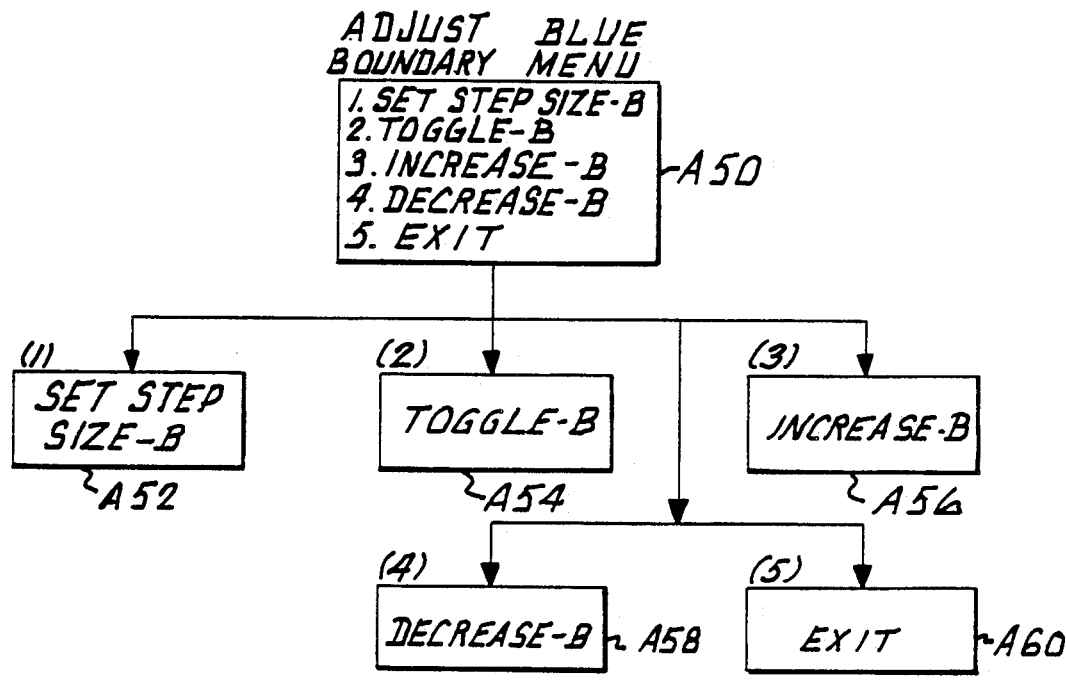
FIG. 20 is a functional flow chart of the blue boundary adjustment menu of the blue boundary screen illustrated in FIG. 17.
Figure 21:
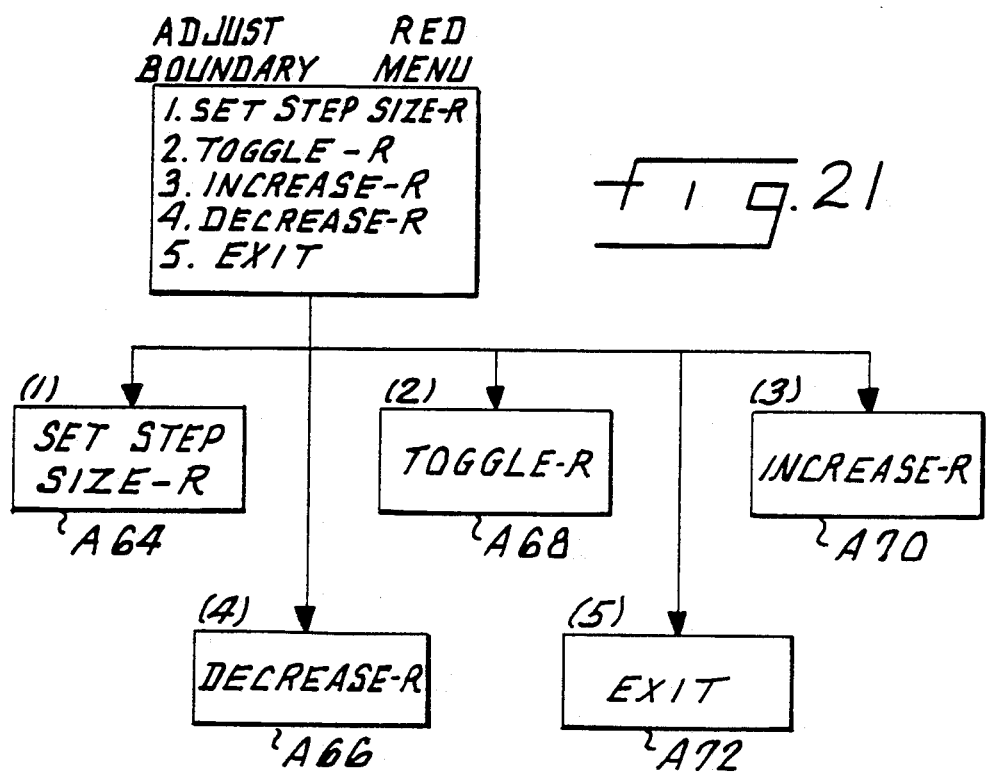
FIG. 21 is a functional flow chart of the red boundary adjustment menu of the red boundary screen illustrated in FIG. 17.

In FIG. 20 a specific case of stained components is demonstrated wherein each of the stained components demonstrates substantially 100% transmittance at the exemplary 500 nm and 620 nm wavelengths, which provides two locations for analysis and thus quantitative analysis of each component.

The above-noted examples clearly indicate and exemplify methods of cell analysis and more specifically, quantitative analysis of cell components with true optical and mass determination. The first monochromatic image above provides a means to provide the quantitative analysis of at least the first component, and the second monochromatic image is invaluable in the identification of other cell components.

The present invention provides both method and apparatus to correlate various stain pairs with the required monochromal optical filters. The two-color camera system is principally used in immunohistochemistry stain applications. These are very often two-color stains, that is the colored antigen/antibody/stain complex vs. cells in tissue compartments without antigen and stained with a counterstain. As it is frequently desired to quantitate either the material counterstained or the antigen/antibody complex, via measurement of cell stain content, it is helpful if at least one of the staining components does not have a spectral overlap at the sensing wavelength of the one of the image sensors. It is preferred to make measurements at approximately the peak transmission value, preferably 100% transmission, as that provides the biggest contrast to the surrounding light spectra and cell components in the cell matrix. Further, the visible light spectrum is not a very broad band region of the total light spectrum, and analysis of cells using a second stain may introduce interference of the overlapping spectra, as these stains tend to be broad band spectra or have broad band spectral outputs. In addition, wide bandpass spectral filters of standard color cameras or sensors contribute to any glare problem during the analysis. Thus, the narrow bandpass filtering reduces an inherent problem of earlier structures. In addition, use of a standard color camera for review of multi-stained cells invites an inherent problem in the output and review of the cells, that is, pixel-to-pixel alignment of the separate images cannot be accommodated as the same regions are not projected in each pixel in the three (usually red, green, blue) colored images provided from a color camera. As a consequence, the images under review are not accurately or consistently reviewed during the analysis, whereas the inventive structure provides for pixel-by-pixel calibration, alignment and cell review.

The image acquisition apparatus noted above provides a means to split or divide the amount of light communicated to each of the individual cameras through the use of a beam splitter, which is preferably a dichroic beam splitter. This attenuation of the light or light transmission may be accomplished at a specific wavelength, as the beam splitter is transparent to a band of wavelengths either above or below the selected wavelength thus allowing that band of light to be transmitted through the splitter; and, it reflects the light beam at the other wavelengths above or below the preselected wavelength and thus limits the band width of the light transmitted to each of the monochromal optical filters. Whether the light beam communicates to the beam splitter is merely split or split at a specific wavelength, the optical filters selectively limit the light transmitted to the cameras to a specific or narrow range of wavelengths for analysis. Provision of a narrow bandwidth light beam to the optical filters improves their efficiency by limiting the background "noise" to be screened from the desired light signal.

Second beam splitter 156 may be exemplary of a dichroic beam splitter, and, for example, may provide transmission of all wavelengths of light above 550 nanometers and reflect all wavelengths below 550 nanometers. Therefore, marking a cell, such as those selected from a patient for cancer analysis, by utilizing one of the above-noted stain combinations will cause the first stain to mark the nucleus and the second stain to mark the associated protein at a protein site. Individual light beams at different specific wavelengths for the stained cell are consequently provided to the first and second camera. Thus, each of the individual components after appropriate optical filtering are analyzed at one of the first and second channels, which is dependent on the light at a wavelength either transmitted or reflected thereto. The electronic light signal from the camera is transmitted to the computer analysis system for conversion to a digital signal, storage and analysis of each of the first and second channel signals and/or combination of these two individual signals or figures for comparative analysis in an overlapping array.

Figure 30:
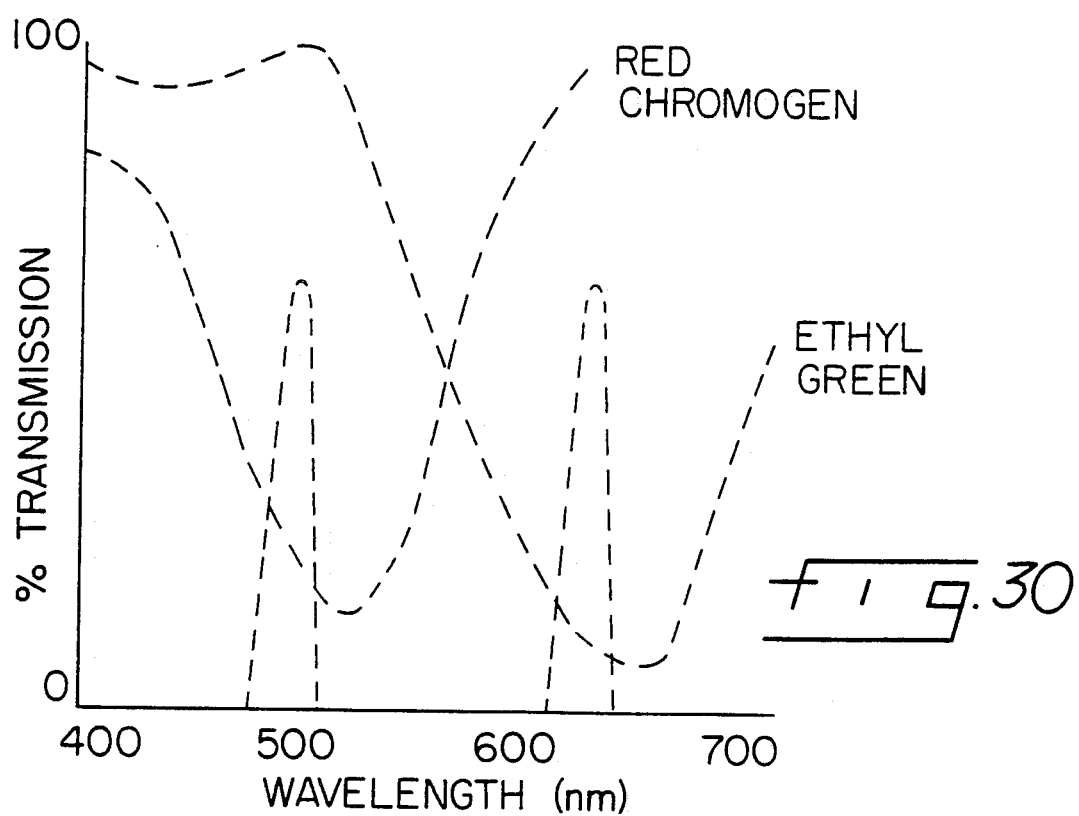
FIG. 30 is a graphical representation of a dual-stain cell spectra transmission.

The two-color camera analytical system of the present invention is matched to the staining spectra of readily available, common acid-base and immunohistochemical stains. The spectral wavelengths chosen match at least one region of 100% transmission of one paired stain component. At the same time, the narrow bandpass filters reduce glare. This is important for purposed of accurate densitometry measurements of the stained substance. By comparison the sensing spectra of typical solid state ordinary "color" cameras use three broad band spectra (these are chosen to match the color visual receptors of the human eye). These overlap with the broad-band, two component, cell staining spectra, e.g., FIGS. 8, 29, and 30; and the wide bandpass spectral filters of the standard color cameras contribute to glare. In addition, the color filtering of standard color cameras occurs on separate pixels (different lines of video) on the solid state sensing chips. Thus, the pixels are not from the same regions in the three-colored images of a color camera.

It is apparent, as noted above, that the mere enhancement of a cell or cell component by staining has been known for quite some time; and further, that the various components of individual cells react or respond to different stains and staining techniques. Past efforts at cell analysis have generally been limited to single camera apparatus or complex analysis of broad band spectra across the total visible light spectrum. The present invention provides a relative "balancing" of the available stains, the spectra of the light transmitted, the optical filters and beam splitters, which all cooperate to provide attenuated or more easily analyzed signals. Thus, a complete system is provided which matches the reagent, the camera, the special software analysis procedure, as well as the hardware related to the computerized network. The monochromal optical filters 164, 166 and second beam splitter 156 are removable for replacement with alternative filters and beam splitters to more readily match the wavelengths for analysis of specific cell components, which are marked by appropriate staining and spectra. Therefore, it can be seen that the above-noted, two-color stain system and dual color sensor system, which is a narrow band-pass filter system, used to provide a light signal, which is measured for optical density and correlated to known conditions for both quantitative as well as qualitative analysis.

All of the chromogens that are presently known for use in staining are wide band pass chromogens and do not provide the narrow band pass that would make analysis, if not easier, at least more readily accessible, thus requiring the steps utilized to screen or filter the overlapping light signals. The stain agents are distinct markers selected to be nonreactive with each other when two or more stains are utilized for simultaneously staining the same cell. One of the problems associated with the use of cameras and electronic equipment is the required effort to maximize the signal intensity at the measured wavelength to overcome or minimize the electrical noise. If the electronic gain is increased for the individual electronic apparatus, the sensors or cameras in this case, the noise ratio or level would also increase. The present apparatus was, therefore, provided without utilizing video camera with a "white clip", which is known to minimize the level of the power or intensity of the output signal. Consequently, all of the light intensity and response is provided through the optical system to the cameras of the present invention.

Initial Equipment Calibration

Calibration, adjustment, alignment and/or focus of the present two-camera apparatus is required prior to its use as an analytical tool. In the alignment procedure, a calibration or reference slide with a grid pattern is mounted on the microscope stage. The grid pattern may take the form of crosshatched lines separated by approximately 0.01 mm, which define a matrix or pattern of small squares. Thereafter, the reticule cross-hair of the microscope, usually visible through the ocular lens, is centered or aligned with the heavy centerlines of the grid pattern, which generally provides centering of the object in the microscope. The microscope is focused by adjustment of the microscope diaphragm with the microscope in focus, centered, and just at the edge of the field-of-view.

After the above-noted initial steps, the microscope eyepiece [not shown] is removed from the apparatus 18. Mirrors 160 and 162 on their pedestal mounts 436, 438, respectively, are rotated in pockets 422, 424. Mirror 160 is rotated to reflect the optical beams back through the focusing lens 154 to the top of the objective diaphragm [not shown]. Rotation of mirror 160 will move the reflected beam up and down across the objective diaphragm. Adjustment of screws 120 in threaded bores 418 of the mounting securing beam splitter 25 will adjust the position of the beam to transmit it through the center of the objective lens. A blocking target or mask is interposed between the transmitted or reflected second and third light beams 157 and 159 in front of cameras 168, 170, which beams 157, 159 impinge on this target. First mirror 160 is rotated to reflect the beam to second mirror 162, which second mirror 158 through second beam splitter 156. Mirrors 160 and 162 are thereafter secured in position by the locking screws 430.

Beams 157 and 159 should by noticeable on the noted target or mask. First mirror 160 should be rotated such that the beam to camera 170 is a full circle and not "clipped," on either the left or right side. If the beam is clipped on the top or bottom, first beam splitter 25 must be adjusted by rotating screws 420 until the beam is centered. Thereafter, first mirror 160 should be locked or secured in place. The optical equipment should not be contacted by fingers during the adjustment period. Similarly, second mirror 162 is rotated to provide an unclipped image to the mask, and first beam splitter 25 is adjusted to properly center the third beam. Subsequently, second mirror 162 is likewise secured by locking screws.

The target can now be removed, and the grid image will be projected on face plate 175 for centering. The elevation or vertical alignment of the projected image on face plate 175 of second camera 170 may be centered by rotation or adjustment of locking screws 480, 482 and 484 of second beam splitter 156. Adjustment of the grid image on face plate 175 across its horizontal plane, that is, left to right, is accommodated by rotation of second beam splitter 156. Adjusting screw 192 securing locking washer 488 is loosened, and turning adjustment screw 493, which contacts the beam splitter mounting pedestal 450, moves pedestal 450 in recess 440. After proper alignment, securing screw 492 may again be tightened to secure washer 488. The grid image, which is generally red, on face plate 173 of first camera 168 may be adjusted by adjustment of screws 501 and 503 on the reverse side of third mirror 158. Bottom screw 503 will move the image left and right across the face plate 173, whereas top screw 501 will adjust the image vertically up or down and will also rotate the image slightly. Thus, screws 501, 503 are utilized to center the image on face plate 173. It is noted that rotation of the image will require repetition of the earlier adjustment of the first beam splitter 25 and also correct centering of the grid image on face plate 175 of second camera 170.

If finer adjustment of the coupler is required, an adjustment cover is placed on the apparatus 18, and, if removed, the eyepiece is returned to the coupler. The grid slide is focused and centered in the eyepiece. Access to front and back rotation lock screws 604 and 582 of second camera 170 is provided through the alignment cover. These screws are loosened and the image from second camera 170 is displayed on monitor 37. Thereafter, second camera 170 is slidably moved along its axis 171 until the monitor image is properly focused. Subsequently, locking screws 600 for first camera 168 are loosened, and the image from first camera 168 is displayed on monitor 37. First camera 168 is similarly slidably moved along its longitudinal axis 169 to focus the image on monitor 37. Locking screws 600 are thereafter tightened, and cameras 168, 170 are now in parfocus. The image on monitor 37 from first camera 168 is centered by adjustment of screws 501 and 503 on third mirror 158. In this adjustment, there should be an equal number of lines on either side [and top to bottom] of the center heavy lines of the grid pattern. The image from second camera 170 is again displayed on monitor 37 and this image is centered by rotation of adjusting screws 480, 484 and 484 of second beam splitter 156 for left-to-right adjustment. Vertical adjustment of the image from camera 170 is again provided by loosening screw 192 and rotating adjusting screw 493 to adjust pedestal 450 in recess 440 prior to resecuring screw 492. The projected grid image is again checked for proper alignment in both vertical and horizontal directions. The images from both first camera 168 and second camera 170 are now projected on monitor 37, and the images are aligned such that there is no greater than ¼ line width of grid pattern between the superimposed images. Vertical and horizontal adjustments are provided by adjusting screws 501 and 503 of third mirror 158, whereas rotational adjustments are made by physically rotating second camera 170. Second camera 170 is rotated until the grid lines of both images are parallel, however, care must be utilized to avoid changing the focus of second camera 170. Both front and back rotation lock screws 604, 582, respectively, are thereafter secured to maintain second camera 170 from further rotation. Third mirror 158 is now adjusted to provide vertical and horizontal alignment of the grid on the monitor. The rotational and vertical-horizontal adjustment may require repetition to achieve proper alignment. The grid slide on the microscope is now moved to a clear area, and the microscope diaphragm is adjusted for proper focus, size and centering. A proper light intensity is provided by attaining a reading of approximately, 200, which is a comparative gray-scale reading on the second camera 170, and the gain adjustment 604 of first camera 168 is adjusted to similarly give a light reading of 200. The apparatus cover 402 is reinstalled and the apparatus is prepared and ready for operation.

It is further considered that the above apparatus is equally applicable to a fluorescent antibody stained cell. As an example, when infectious agents such as viruses and bacteria, and other antigenic materials which are principally of a protein nature, invade body tissue, soluble substances are produced which specifically react with these alien materials. The soluble substances are called "antibodies" and materials which elicit their production and called "antigens". Antibodies can be coupled to fluorescent dyes such as Fluorescin. Antibodies labeled by fluorescent dyes are called "fluorescent antibodies" and are utilized as immunospecific stains for the detection of antigens in cells and tissues. The marked regions in a cell are seen as a characteristic color when the cell section is examined with a fluorescent microscope. This method of fluorescent microscopy may also be operable with the above-noted apparatus. Transmission microscopy was utilized for the examples in the particular description noted above. However, it is appreciated that the present apparatus may be applicable to the fluorescent microscopic analysis at specific wavelengths. A proper staining agent must be utilized to mark either the nucleus and/or protein at a selected protein site when either the fluorescent or transmission microscopy techniques are utilized with the apparatus and system of the present invention.

While only specific embodiments of the invention have been described and shown, it is apparent that various alterations and modifications can be made therein. It is, therefore, the intention in the appended claims to cover all such modifications and alterations as may fall within the scope and spirit of the invention

What is claimed is:

1. A method of analyzing cells, having at least a first cellular component and a second cellular component, said method comprising:
   chemically-optically enhancing the cells with a first and a second spectral stain material,
   each of said first and second spectral stain materials combining with one of said first and second cellular components to form a first cell combination and a second cell combination,
   said first cell combination having a maximum optical transmittance at a first predetermined wavelength and a lower optical transmittance at a predetermined second wavelength,
   said second cell combination having a substantial light absorption at said first predetermined wavelength,
   transmitting an image of at least the first and second cell combinations, and communicating said image to a beam splitter;
   splitting said image into a first image and a second image;
   filtering the first image with a first filter to provide a first substantially monochromatic image at said first wavelength;
   filtering the second monochromatic image with the second filter to provide a second substantially monochromatic image at said second wavelength;
   sensing the filtered first monochromatic image with a first sensing means to provide a first electrical output representative of the first monochromatic image;
   sensing the filtered second monochromatic image with a second sensing means to provide a second electrical output representative of the second monochromatic image; and,
   providing an analysis of characteristics of the cells at a characteristic analyzer based on the electrical outputs from the first and second sensing operations.

2. A method of analyzing cells as claimed in claim 1 and further in which the step of splitting said image in a first and a second images includes providing each said first and second images with different spectral wavelength bandwidths.

3. A method of analyzing cells as claimed in claim 1 and further comprising:
   analyzing quantitatively said first monochromatic image for an associated one of said first and second cell components and identifying the other of said first and second cell components utilizing said second monochromatic image.

4. A method of analyzing cells as claimed in claim 3 and further comprising:
   measuring the optical density of said associated one of said first and second cell components of said first monochromatic image to provide said quantitative analysis.

5. A method in accordance with claim 1 wherein the step of chemically-optically enhancing the cells with first and second materials comprises treating said cells with a monoclonal antibody stain.

6. A method in accordance with claim 2 further comprising the steps of processing the electrical signals from each sensing means separately to provide cell analysis information and also combining the information from both sensing means to provide a quantitative analysis of the examined cells.

7. A method of analyzing cells as claimed in claim 6 and further comprising:
   providing a means for displaying any of said first image said second image and said combined image; and
   coupling said display means to said means for analyzing to receive said sensed images.

8. An apparatus for the analysis of cells with at least a first cellular component and a second cellular component, a first spectral material and a second spectral material, one of said first and second cellular components chemically combining with one of the first and second spectral materials to provide a first cell combination and the other of said first and second cellular components chemically combining with the other of said first and second spectral materials to provide a second cell combination, said first cell combination having approximately maximum optical transmittance at a first predetermined wavelength and a lower optical transmittance at a second predetermined wavelength, said second cell combination having substantial light absorption at said first predetermined wavelength, said apparatus comprising:
- a source for projecting light on said cell;
- means for forming and magnifying an image of the first and second cell combinations and for communicating the image;
- means for splitting the communicated image into a first image and a second image;
- first means for filtering the first image to provide a first substantially monochromatic image at said first wavelength;
- second means for filtering the second image to provide a second substantially monochromatic image at said second predetermined wavelength;
- first means for sensing the first monochromatic image and providing a first electrical output representative thereof;
- second means for sensing the second monochromatic image and providing a second electrical output representative thereof; and,
- means for analyzing said cell combinations and thus said cells, which analysis means is operable to receive and store the respective first and second sensing means electrical outputs, to combine said first and second images to provide an analysis therefrom, and to provide an output about at least one cell characteristic.

9. An apparatus for the analysis of cells as claimed in claim 8 wherein said means for analyzing further comprises a means for displaying said first image, said second image, said combined first and second image and said analysis thereof.

10. An apparatus for the analysis of at least one cell, which cell has at least a first cellular component and a second cellular component, one of said first and second components chemically-optically enhanced by combining with one of a first spectral material and a second spectral material to define a first cell combination, the other of said first and second cellular components chemically-optically enhanced by combining with the other of said first and second spectral materials to define a second cell combination, one of said first and second cell combinations having approximately a maximum transmittance at one of a first and second predetermined wavelength and a lower transmittance at the other of said first and second wavelengths, and the other of said first and second cell combinations having substantial light absorption at said first predetermined wavelength, said apparatus comprising:
- means for providing a magnified image of at least the first and second cellular components in a magnified component image light beam with a continuous spectrum;
- means for acquiring said magnified image;
- said image acquiring means having means for reflecting said magnified component image light beam, means for splitting said magnified component image light beam into at least a first and a second light beam, means for monochromatically filtering said first and second light beams, and, a first sensor and a second sensor operable to receive monochromatic light beams and provide an electrical output signal based on said monochromatic light beams;
- said beam splitter means operable to receive said component image light beam and transmit a first light beam and a second light beam;
- said first and second light beams communicated to said first and second sensors through said filter means, which filter means are optically matched to said first and second cell combinations and said predetermined first and second wavelengths to filter said first beam to provide one of said first and second sensors approximately a monochromatic fist light beam at approximately one of said first and second predetermined wavelengths, and approximately a monochromatic second light beam at approximately the other of said first and second predetermined wavelengths to the other of said first and second sensors,
- each of said first and second sensors operable to provide an electronic signal indicative of said monochromatic images; and,
- means for digitizing and storing an electrical signal for each of said first and second light beams, which digitizing means is operable to receive said electrical output signals from said first and second sensors to digitize, combine, store and project said first and second light beam signals for review and analysis of said cell.

11. An apparatus as claimed in claim 10 further comprising means for reflecting; said means for beam splitting having a first beam splitter providing a split path for the magnified component light beam and a second beam splitter, which first beam splitter and reflecting means cooperate to communicate said magnified image light beam to said second beam splitter;
- said second beam splitter having a predetermined splitting wavelength operable to split said magnified light beam image into a first light beam below said predetermined splitting wavelength and a second light beam above said predetermined splitting wavelength for communication to said first and second sensors;
- said filter means operable to filter said first light beam and second light beam communicated to said first and second sensors at said predetermined first and second wavelengths, one of said first and second wavelengths approximately at the maximum optical transmittance of the first and second light beams.

12. An apparatus as claimed in claim 11 wherein said filter means are a first monochromatic optical filter operable to filter and first light beam at approximately said first predetermined wavelength and a second monochromatic optical filter operable to filter and said second light beam at approximately said second predetermined wavelength, which filtered first and second light beams are communicated to said first and second sensors, respectively.

13. An apparatus as claimed in claim 12 wherein said first and second sensors comprise a first video camera and a second video camera;
- said fist camera positioned and operable to receive said filtered first light beam, and said second camera positioned and operable to receive said filtered second light beam, which first and second cameras are operable to provide an electrical output representative of said image at said first and second wavelengths, respectively.

14. An apparatus as claimed in claim 13 wherein said reflecting means comprises a first mirror, a second mirror and a third mirror;

said image acquisition apparatus further comprising a focusing lens, which lens is interposed between said first mirror and said first beam splitter to provide a focused and magnified image cell component light beam to said first mirror; and, said second mirror is operable to receive and communicate said focused and reflected first light beam image from said first mirror to said second beam splitter.

15. An apparatus as claimed in claim 14 wherein said third mirror is positioned and operable to reflect said first beam from said second beam splitter to said first sensor.

16. An apparatus as claimed in claim 15 wherein said second beam splitter, said third mirror and first sensor cooperate to define a first communication path distance therebetween for said first light beam; said second beam splitter and said second sensor cooperate to define a second communication path distance therebetween for said second light beam, which first and second communication path distances are approximately equal.

17. An apparatus as claimed in claim 13 wherein said first sensor has a first longitudinal axis, which first sensor is movable along said first axis to focus said first sensor and one of said filtered first and second light beam image in said digitizing means; and said second sensor has a second longitudinal axis, which second sensor is movable along and rotatable about said second axis to focus said second sensor and the other of said first and second light beam image in said digitizing means.

18. An apparatus as claimed in claim 17 wherein said first sensor and second sensor further comprise a first electronic gain adjust and a second electronic gain adjust, respectively, to focus said first and second light beam image in said digitizing means.

19. An apparatus as claimed in claim 17 further comprising a housing;

said housing having a top panel, a front panel, rear panel, a bottom panel, and a first and a second sidewall, which cooperate to define a chamber for said image acquisition means;

said first beam splitter including a focus lens mounted in said housing; and said reflecting means, said first and second monochromatic optical filters, said second beam splitter, and said first and second sensors are adjustably mounted in said housing.

20. An apparatus as claimed in claim 19 further comprising a first mirror mounting base and a second mirror mounting base, each base having a generally cylindrical first pintle and second pintle for said first and second mounting base, respectively;

said first mirror and said second mirror mounted and operable on said first mounting base and second mounting base, respectively;

said bottom panel defining a horizontal reference plane and, a first pivot socket and a second pivot socket to receive said first and second mounting base pintles, and, a first threaded bore and a second threaded bore open to said first and second pivot sockets, respectively;

said first pintle positioned and rotatable in said first pivot socket and said second pintle positioned and rotatable in said second pivot socket to rotatably adjust said first mirror and second mirror, respectively, for reflecting said magnified component beam from said first beam splitter to said second beam splitter; and, a first threaded locking screw and a second threaded locking screw matable with said first threaded bore and second threaded bore, respectively, to contact said pintles and secure said pintles and mirrors in position.

21. An apparatus as claimed in claim 20 further comprising a means for adjusting said second beam splitter, which adjusting means has a mounting frame and a gimballed base;

said second beam splitter mounted and operable in said frame, which frame defines at least a first, a second and a third through-hole;

said bottom panel defining a washer well having a first threaded and generally centered bore and, a recessed seat with a sidewall and a second threaded bore, said recessed seat operable to receive said gimballed base which is adjustable therein, and a threaded locking passage;

said gimballed base defining a generally centrally located cavity and, a first, a second and a third threaded base bore, and a pivot passage alignable with said recessed seat second threaded bore;

a spherical bearing mounted in said centrally located cavity;

a first, a second and a third threaded means for securing, and a threaded pivot means for securing;

a first, second and third vertical biasing means positioned between said frame and gimballed base and aligned with said first, second and third base threaded bores, said mounting frame and second beam splitter positioned on said gimballed base with said first, second and third through-holes aligned with said first, second and third threaded gimballed base bores and vertical bias means to receive said first, second and third threaded securing means to mate, respectively, with said first, second and third threaded base bores to secure said frame and second beam splitter against the bias of said vertical biasing means; said threaded pivot means for securing extending through said gimballed base pivot passage and threadably engaging said recessed seat second threaded bore;

a lateral bias means positioned and operable between said recessed seat sidewall and gimballed base to pivotably bias said base in said recessed seat about said threaded pivot securing means;

a third locking screw to control the rotation of said gimballed base positioned and operable in said threaded locking passage to contact said gimballed base positioned in said recess opposite said lateral biasing means;

a washer with a washer through-bore;

a threaded means for securing said washer;

said washer positioned in said washer well with said washer through-bore aligned with said washer-well threaded bore to receive said washer securing means; said washer contacting said laterally biased gimballed base, and cooperating with said threaded pivot securing means and said third locking screw to secure said base at a fixed position with said washer and washer securing means against rotational movement by said lateral biasing means.

22. An apparatus as claimed in claim 21 further comprising a generally vertical member and a second gimballed mounting having a lower section with at least a first and a second mounting bolt port; said third reflecting mirror mounted on said vertical member;

a pair of bolts for securing said second gimbal;

said bottom panel defining at least a first threaded gimbal port and a second threaded gimbal port;

said gimballed mounting lower section first and second bolt ports aligned with said bottom panel first and second threaded gimbal ports, to receive one of said pair of second gimbal bolts, respectively, which bolts secure said second gimbal mounting assembly to said bottom panel;

said gimbal vertical member defining a first and a second threaded adjustment port, which adjustment ports are both vertically and horizontally offset from each other;

a first threaded adjustment member and a second threaded adjustment member, which first and second threaded adjustment members are positioned in said first and second adjustment ports, respectively, and operable to contact and adjust said third mirror both vertically and horizontally, to reflect and communicate said first beam from said second beam splitter to said first sensor.

23. An apparatus as claimed in claim 22 further comprising a first monochromatic optical filter mounting frame and a second monochromatic optical filter mounting frame;

each of said frames further defining means for receiving and retaining said optical filters therein;

each of said frames defining a first mounting bolt bore and a second mounting bolt bore;

a pair of threaded bolts for each of said first and second frames;

said bottom panel defining a pair of first filter threaded bolt holes, and a pair of second filter threaded bolt holes, which bolt holes are alignable with said first and second filter frame bores, respectively, to receive said threaded bolts to secure said frames to said bottom panel.

24. An apparatus as claimed in claim 23 wherein each of said frame means for retaining and securing said optical filters is a slotted frame.

25. An apparatus for the analysis of at least one cell, each of said cells having at least one nuclear DNA with a nucleus, that is chemically-optically enhanced by a first spectral stain material, and at least one protein and associated protein site, that is chemically-optically enhanced by an immunohistochemical spectral stain material, said stained nucleus having approximately maximum optical transmittance at a first predetermined wavelength and a lower optical transmittance at a second predetermined wavelength, said stained proteins at said protein sites having a substantial light absorption at said first predetermined wavelength, said apparatus comprising:

means for providing a magnified objective image of said at least one cell in a magnified cell component;

means for acquiring said magnified image;

said image acquiring means having means for beam splitting said magnified image, means for reflecting said image, means for monochromatically filtering light beams and at least a first sensor and a second sensor each operable to receive a monochromatic light beam and provide an analog electrical output signal representative of said sensed monochromatic light beam;

said image from said magnifying means comprising a plurality of wavelengths encompassing a broadband spectrum from one of the visible and infrared light ranges;

said beam splitter means operable to receive said magnified cell component light beam and transmit a first light beam below a predetermined splitting wavelength and a second light beam above said splitting wavelength to said first and second sensors, respectively, through said monochromatic filter means, which monochromatic filter means are operable to filter said first and second light beams at said first and second predetermined wavelengths to provide said first and second sensor a monochromatic first light beam at approximately said first predetermined wavelength and a monochromatic second light beam at approximately said second predetermined wavelength to the other of said first and second sensors; and, means for digitizing and storing an analog signal for each first and second light beams, which digitizing means is operable to receive said analog electrical output signals from said first and second sensors to digitize, combine, store and project said first and second light beam signals for review.

26. An apparatus as set forth in claim 12 wherein said first optical filter is an optical bandpass filter operable to filter a light beam at a wavelength of about 620 nanometers.

27. An apparatus as set forth in claim 26 wherein said first optical filter is an optical bandpass filter operable to filter a light beam at a wavelength between about 610 nanometers and 630 nanometers.

28. An apparatus as set forth in claim 12 wherein said second optical filter is an optical bandpass filter operable to filter a light beam at a wavelength of about 500 nanometers.

29. An apparatus as set forth in claim 28 wherein said second optical filter is operable to filter a light beam at a wavelength between about 490 and 510 nanometers wide.

30. An apparatus as claimed in claim 12 wherein said second beam splitter is a dichroic beam splitter.

31. An apparatus for the analysis of cells as claimed in claim 8 wherein said first spectral material is one of a thionin and a red chromogen activated by alkaline phosphatase, and the second spectral material is the other of said thionin and red chromogen.

32. An apparatus for the analysis of cells as claimed in claim 31 wherein one of said first and second cellular components is a DNA nucleus and said thionin is operable to combine with and distinguish said DNA nucleus in said cell.

33. An apparatus for the analysis of cells as claimed in claim 31 wherein one of said first and second cellular components is selected from among the group comprised of proteins, hormones and lipids, and said red chromogen and alkaline phosphatase is operable to combine with and distinguish said one component for said analysis.

34. An apparatus for the analysis of cells as claimed in claim 8 wherein said first spectral material is one of methyl green and diaminobenzidene with peroxidase, and the second spectral material is the other of said methyl green and diaminobenzidene with peroxidase.

35. An apparatus for the analysis of cells as claimed in claim 34 wherein one of said first and second cellular components is a DNA nucleus and said methyl green is combinable with said nucleus to chemically-optically enhance said DNA nucleus in said cell.

36. An apparatus for the analysis of cells as claimed in claim 35 wherein the other of said first and second components is selected from among the group of proteins, hormones and lipids, and said diaminobenzidene with peroxidase is combinable with said other component for chemical-optical enhancement for analysis.

37. An apparatus for the analysis of cells as claimed in claim 8 wherein said first spectral material is one of methyl green and red chromogen with alkaline phosphatase, and the second spectral material is the other of said methyl green and red chromogen.

38. An apparatus for the analysis of cells as claimed in claim 37 wherein one of said first and second cellular components is a DNA nucleus combinable with said methyl green for chemical-optical enhancement of said DNA nucleus in said cell.

39. An apparatus for the analysis of cells as claimed in claim 37 wherein one of said first and second cellular components is selected from among the group comprised of proteins, hormones and lipids and is combinable with said red chromogen with alkaline phosphatase for chemical-optical enhancement of said one component for analysis.

40. A method of calibration for an apparatus utilizing two solid state sensors in the image analysis of cells, said method comprising:
providing means for analyzing cells, which analyzing means has a microscope with a cell examination location, at least one beam splitter, a first optical filter, a second optical filter, means for projecting light through said cell, and a means for providing a cell characteristic;
providing a calibration pattern to be viewed by a microscope at the examination location of the cells;
projecting a light beam through said pattern to provide an image;
acquiring an image of the pattern and communicating the image to a beam splitter;
splitting the image into first and second images of the pattern;
sensing the first image by the first sensor and providing a first electrical output representative of the first image of the pattern;
sensing the image of the pattern by a second sensor and providing a second electrical output representative of the second image pattern, each of said first and second electrical outputs communicated to said means for providing a cell characteristic;
combining and displaying the first and second pattern images overlying one another; and
adjusting the sensor positions to align the overlying patterns to provide a substantially pixel-by-pixel alignment of the image patterns being sensed by the first and second sensors.

41. A method of calibration in accordance with claim 40 further comprising providing a grid pattern for said pixel-by-pixel alignment and including the step of overlying the grid image from one of said first and second sensors over the second grid image from the other of said first and second sensors.

42. A method of calibration in accordance with claim 41 further comprising adjusting at least one of said first and second sensors until the first and second grid images are substantially aligned one over the other.

43. An apparatus as claimed in claim 25 wherein said immunohistochemical staining material contains a specific antigen.

44. An apparatus as claimed in claim 43 wherein said immunohistochemical staining material has a monoclonal antibody against said specific antigen.

45. An apparatus as claimed in claim 44 wherein said immunohistochemical staining material includes staining with an alkaline phosphatase compound.

46. An apparatus as claimed in claim 25 wherein said means for providing a magnified image further comprises a mounting stage, which mounting stage is operable to receive a specimen holder.

47. An apparatus as claimed in claim 46 wherein said specimen holder is operable to retain an alignment grid for said first and second cameras, which grid has a predetermined matrix.

48. An apparatus as claimed in claim 47 wherein said grid is a matrix of a plurality of horizontally and vertically aligned squares approximately 0.01 millimeters on a side.

49. An apparatus as claimed in claim 46 wherein said first and second sensors each have a means for adjusting said sensors, which adjusting means is operable to adjust the focus and magnification of said sensor output.

50. An apparatus as claimed in claim 49 wherein said adjusting means includes a rotational adjustment and a translational adjustment for aligning said patterns on said first and second sensors.

51. An apparatus as claimed in claim 5 wherein said first and second sensors are monochromatic video cameras.

52. A method as claimed in claim 1 further comprising projecting light through said cell from a means for projecting light and forming a cell image.

53. A method in accordance with claim 1 including the step of transmitting light in wavelengths between 400–700 nm and using marrow band filters of about 20 nm for filtering.

54. A method as claimed in claim 8 in which the first filter is substantially matched to said first wavelength and the second filter is substantially matched to said second wavelength.

55. A method in accordance with claim 1 including the step of combining a fluorescent spectral stain material with a first cellular component and using a fluorescent microscope for the analysis thereof.

* * * * *

UNITED STATES PATENT AND TRADEMARK OFFICE
CERTIFICATE OF CORRECTION

PATENT NO. : 4,998,284

DATED : March 5, 1991

INVENTOR(S) : Bacus, et al.

It is certified that error appears in the above-identified patent and that said Letters Patent is hereby corrected as shown below:

On the title page:

Under the heading "U.S. Patent Documents", change "Matshushita et al." to --Matsushita et al.--.

Under "Other Publications", change "Steriod" to --Steroid--.

Under "Other Publications", change "Green et al." to --Greene et al.--.

Column 3, Line 10, after "available" change "t" to --to--.

Column 3, Line 50, after "desirable" insert --to--.

Column 4, Line 26, change "equality" to --quality--.

Column 9, Line 51, change "measuring" to --measure--.

Column 11, Lines 22-23, change "stain-stain" to --stain-cell--.

Column 11, Line 68, change "biotinalated" to --biotinylated--.

Column 12, Line 17, delete "," (comma).

Column 13, Line 39, change "A" to --α--.

Column 16, Lines 33-34, change "abovedescribed" to --above-described--.

UNITED STATES PATENT AND TRADEMARK OFFICE
CERTIFICATE OF CORRECTION

PATENT NO. : 4,998,284

DATED : March 5, 1991

INVENTOR(S) : Bacus, et al.

It is certified that error appears in the above-identified patent and that said Letters Patent is hereby corrected as shown below:

Column 17, Line 50, change "16" to --164--.

Column 18, Line 17, after "X" insert --+--.

Column 21, Line 59, change "adjusting" to --adjustment--.

Column 22, Line 13, change "is" to --its--.

Column 23, Line 17, change "Combining" to --Combined--.

Column 23, Line 20, change "Chromagen" to --Chromogen--.

Column 23, Line 26, change "Chromagen" to --Chromogen--.

Column 24, Line 23, change "chromagen" to --chromogen--.

Column 24, Line 35, change "chromagen" to --chromogen--.

Column 27, Line 46, change "beams" to --beam--.

Column 28, Line 55, change "484" (first occurrence) to --482--.

Column 28, Line 57, change "192" to --492--.

Column 29, Line 14, delete "," (comma) (first occurrence).

Column 30, Line 26, change "images" to --image--.

UNITED STATES PATENT AND TRADEMARK OFFICE
CERTIFICATE OF CORRECTION

Page 3 of 3

PATENT NO. : 4,998,284
DATED : March 5, 1991
INVENTOR(S) : Bacus, et al.

It is certified that error appears in the above-identified patent and that said Letters Patent is hereby corrected as shown below:

Column 30, Line 55, after "image" (first occurrence) insert --,-- (comma).

Column 32, Line 11, change "fist" to --first--.

Column 32, Line 62, change "fist" to --first--.

Column 36, Line 21, change "beams" to --beam--.

Column 38, Line 48, change "marrow" to --narrow--.

Signed and Sealed this

First Day of December, 1992

Attest:

DOUGLAS B. COMER

*Attesting Officer*   *Acting Commissioner of Patents and Trademarks*